(12) United States Patent
Kabakov et al.

(10) Patent No.: US 8,696,578 B2
(45) Date of Patent: Apr. 15, 2014

(54) FETAL HEART MONITORING RANGE

(75) Inventors: Serguei Kabakov, Savage, MD (US);
Bradley Fox, Ellicott City, MD (US);
Steven Mitchell Falk, Baltimore, MD (US)

(73) Assignee: General Electric Company, Schenectady, NY (US)

( * ) Notice: Subject to any disclaimer, the term of this patent is extended or adjusted under 35 U.S.C. 154(b) by 121 days.

(21) Appl. No.: 13/331,197

(22) Filed: Dec. 20, 2011

(65) Prior Publication Data

US 2013/0158406 A1  Jun. 20, 2013

(51) Int. Cl.
*A61B 8/00* (2006.01)

(52) U.S. Cl.
USPC .......................................................... 600/453

(58) Field of Classification Search
USPC .......................................................... 600/453
See application file for complete search history.

(56) References Cited

U.S. PATENT DOCUMENTS

| | | | | |
|---|---|---|---|---|
| 3,982,528 A | * | 9/1976 | Phillipps ........................ 600/453 |
| 4,984,576 A | * | 1/1991 | Schulenberg et al. ........ 600/453 |
| 5,853,005 A | * | 12/1998 | Scanlon ........................ 600/459 |
| 2008/0208057 A1 | | 8/2008 | Hoctor et al. |
| 2010/0168596 A1 | | 7/2010 | Jaeschke et al. |
| 2010/0191118 A1 | | 7/2010 | Kabakov |
| 2010/0191119 A1 | | 7/2010 | Muthya et al. |
| 2011/0098586 A1 | | 4/2011 | Kabakov |
| 2011/0152688 A1 | | 6/2011 | Venugopalan |
| 2011/0160591 A1 | | 6/2011 | Smith et al. |

OTHER PUBLICATIONS

Bhogal, Karnie & Jayawardane, Indu Asanka, Obesity on obstetrics: new challenges and solutions using abdominal fetal ECG, Dec. 2008/Jan. 2009, Midwives Online, http://www.rcm.org.uk/midwives/in-depth-papers/obesity-on-obstetrics-new-challenges-and-solutions-using-abdominal-fetal-ecg/.

Phillips Healthcare, Improving ECG Quality, Published Sep. 2008, Edition 1, United States.

* cited by examiner

*Primary Examiner* — Jonathan Cwern
(74) *Attorney, Agent, or Firm* — Rathe Lindenbaum LLP

(57) ABSTRACT

An approximate distance between an ultrasonic transducer and a fetal heart is determined. A range of distances from the ultrasonic transducer is sensed using the ultrasonic transducer, wherein the range has a minimum distance based upon the approximate distance. A heart rate of the fetal heart is monitored using ultrasonic echo signals from the range.

20 Claims, 15 Drawing Sheets

Table2m. Values x1, x2, y1, y2, z for monitoring mode

| Channel1 TD | Channel2 TD | x1[us] | x2[us] | y1[us] | y2[us] | z[us] |
|---|---|---|---|---|---|---|
| TD3_30 | N/A | 172 | | 212 | 212 | 400 |
| TD3_12 | | 58 | 172 | 98 | 98 | |
| TD6_15 | | | 58 | 136 | 136 | |
| TD9_18 | | | | 174 | 174 | |
| TD12_21 | | | | 212 | 212 | |
| TD15_24 | | | | 250 | 250 | |
| TD18_27 | | | | 288 | 288 | |
| TD21_30 | | | | 326 | 326 | |

Notes:
1) us-microsecond
2) Timing diagram TD3_12 drives penetration depth from 3-12cm
3) Pulse repetition rate (PRR) for monitoring mode is 2.5khz Table1m. Values t1 ... t8, r1 ....r8 for monitoring mode

| t1 | 0 | r1 | t1+y1 |
|---|---|---|---|
| t2 | t1+x1 | r2 | r1+x1 |
| t3 | z | r3 | t3+y2 |
| t4 | t3+x2 | r4 | r3+x2 |
| t5 | 2*z+t1 | r5 | 2*z+r1 |
| t6 | 2*z+t2 | r6 | 2*z+r2 |
| t7 | 2*z+t3 | r7 | 2*z+r3 |
| t8 | 2*z+t4 | r8 | 2*z+r4 |

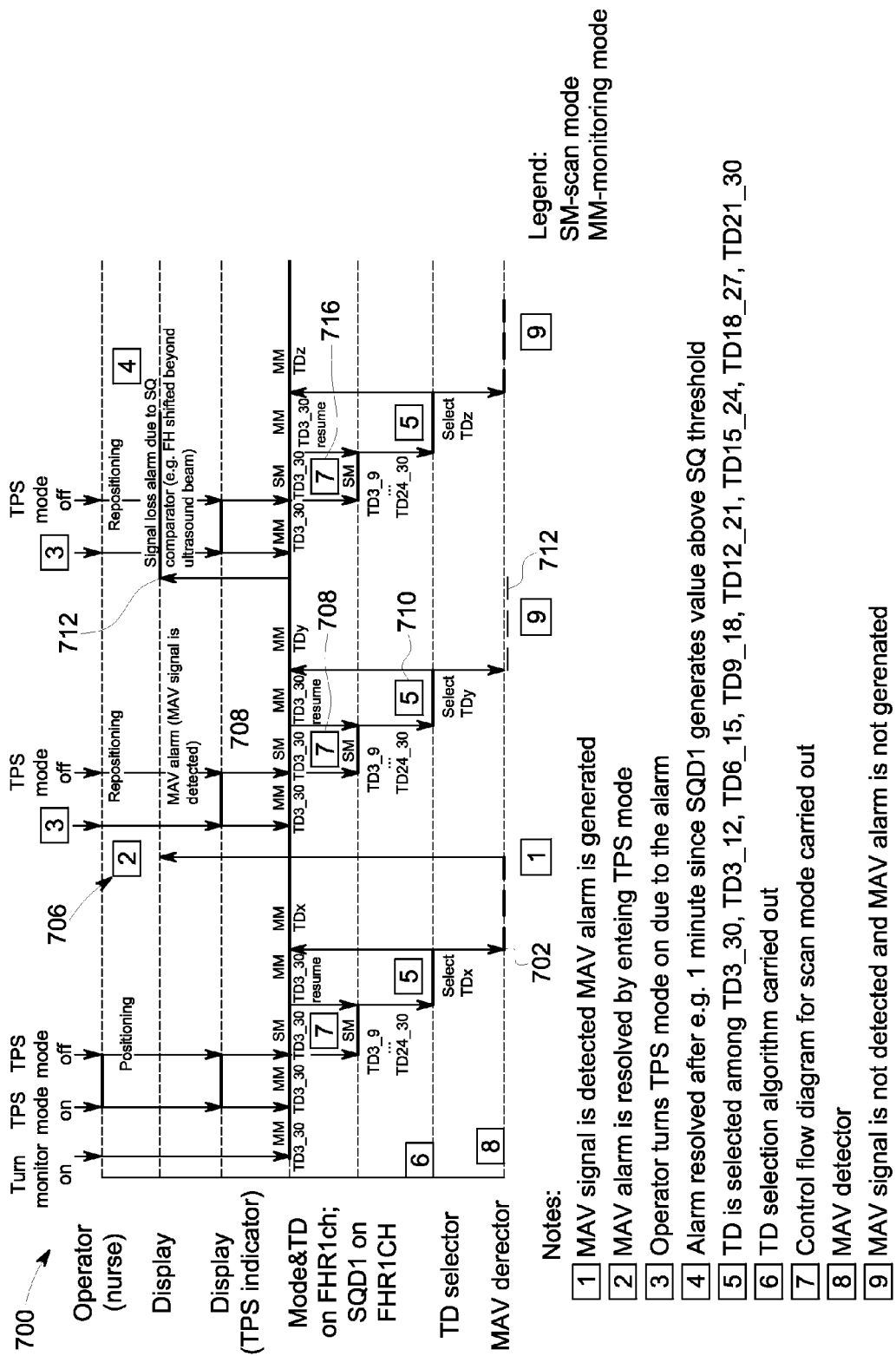

FETAL HEART MONITORING RANGE

CROSS-REFERENCE TO RELATED PATENT APPLICATIONS

The present application is related to co-pending U.S. patent application Ser. No. 13/331,245 filed on the same day herewith by Serguei Kabakov, Steven M. Falk and Bradley Fox, and entitled MATERNAL CONTRIBUTION DETECTION DURING FETAL HEART MONITORING, the full disclosure of which is hereby incorporated by reference.

BACKGROUND

Fetal heart monitors employ ultrasound transducers for measuring physiological parameters of the heart of an unborn child. In some circumstances, abdominal fat may increase a distance between the ultrasound transducer and the fetal heart being monitored. Increasing the penetration depth of ultrasound pulses to accommodate this larger distance may decrease signal-to-noise ratio and may undesirably result in the ultrasound transducer picking up a signal from the maternal abdominal vessels in addition to or in place of a signal from the fetal heart rate.

BRIEF DESCRIPTION OF THE DRAWINGS

FIG. 11 is a control flow diagram of another example method for fetal heart monitoring using a cancellation mode to identify the influence of maternal signals.

DETAILED DESCRIPTION OF THE EXAMPLE EMBODIMENTS

Figure 1:
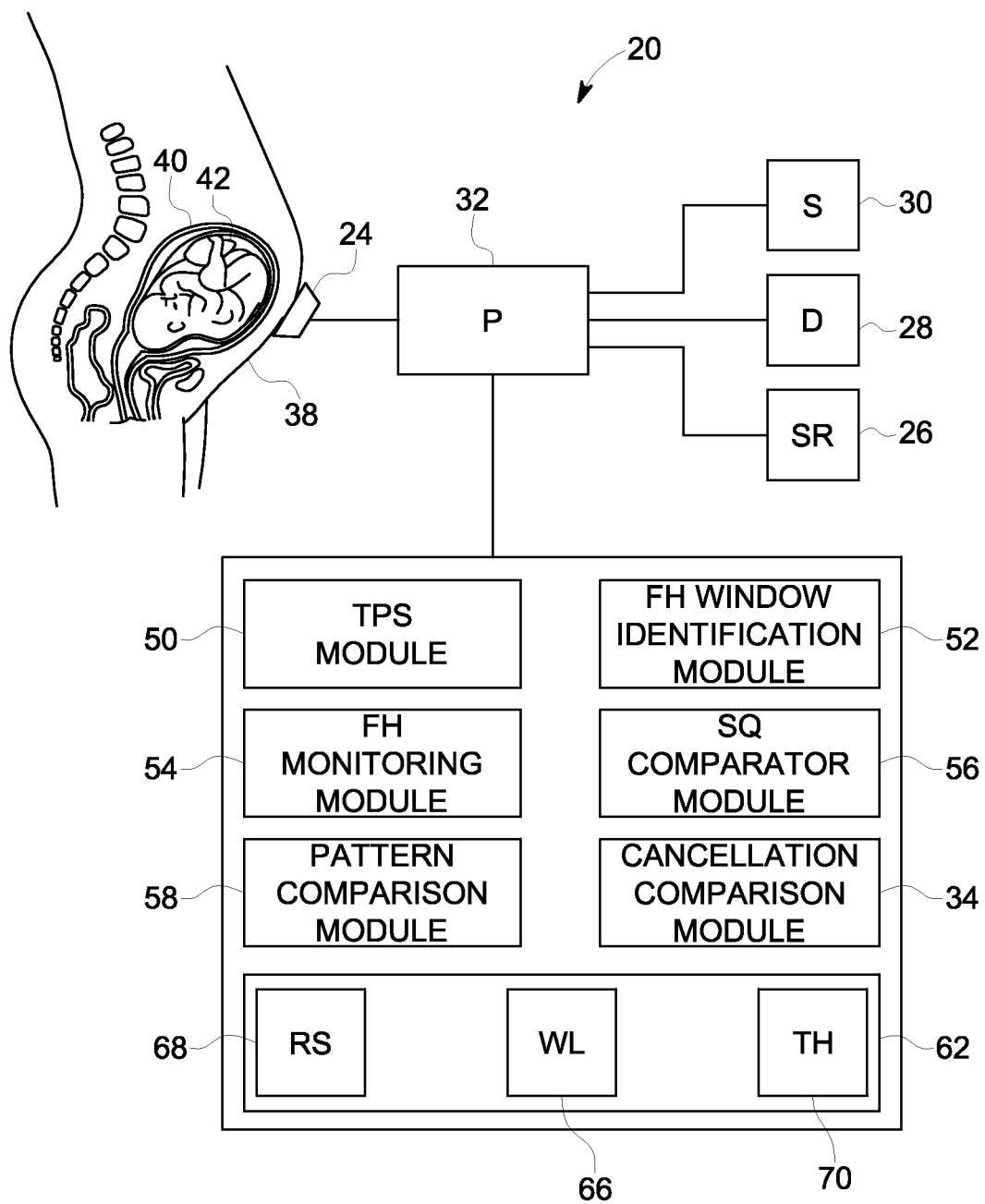
FIG. 1 schematically illustrates one example of a fetal heart monitoring system.

FIG. 1 schematically illustrates an example fetal heart monitoring system 20. As will be described hereafter, fetal heart monitoring system 20 defines a window about the fetal heart which is subsequently used for focused fetal heart monitoring. During ongoing monitoring of the fetal heart by an ultrasound transducer, fetal heart monitoring system 20 uses a reference fetal heart signal to determine whether signals received from the ultrasound transducer are being impacted by pulsations of blood flow through maternal abdominal vessels. As a result, signal-to-noise ratios are maintained and reliability of fetal heart monitoring is enhanced.

Fetal heart monitoring system 20 comprises ultrasound transducer 24, strip recorder 26, display 28, speaker 30, processor 32 and memory 34. Ultrasound transducer 24 (schematically shown) comprises one or more ultrasound transducers, each transducer including an emitter and receiver. Each transducer 24 is configured to be mounted to or supported adjacent the abdomen 38 proximate womb 40 containing an unborn child 42. In one embodiment, ultrasound transducer may be provided as part of an ultrasound probe.

Each transducer 24 is configured to generate ultrasonic waves or ultrasound beams directed towards the unborn child or fetus 42, wherein the waves or beams are reflected from fetus 42 and bounced back to transducer 24. The return ultrasound echoes or ultrasound signals carry information obtained by Doppler shift due to movement of the heart. The information contained in such reflected waves or beams is used by processor 32 to determine a heart rate of fetus 42.

Strip recorder 26, display 28 and speaker 30 (that can be used as an alarm) comprise notification mechanisms that visibly or audibly output information to caregivers. Strip recorder 26 comprises a device configured to print physiological parameters, such as heart rate, determined based upon signals received from transducer 24. Display 28 comprises a monitor, screen or other device by which heart rate information may be visibly presented to a caregiver. Speaker 30 comprises a device configured to output audible information, such as a sound of heartbeats detected by transducer 24. In one implementation, speaker 30 and/or display 28 may be utilized to provide an audible or visible notification, warning or alarm alerting a caregiver of heart rate characteristics or sensed characteristics that warrant concern. In some implementations, fetal heart monitoring system 20 may omit one or more of such output devices 26, 28 and 30 or may comprise additional or alternative output devices.

Processor 32 comprises one or more processing units configured to generate control signals directing the emission and receipt of ultrasound signals using transducer 24, to process and analyze signals received from transducer 24, and to generate control signals directing output to one or more of output devices 26, 28 and 30 based upon the results of such analysis. In some implementations, processor 32 may additionally store such signals in memory 34 for later analysis and may store the analytical results in memory 34. For purposes of this application, the term "processing unit" shall mean a presently developed or future developed processing unit that executes sequences of instructions contained in memory 34. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, parts of processor 30 and memory 34 to may be embodied as part of one or more application-specific integrated circuits (ASICs). Unless otherwise specifically noted, processor 32 is not limited to any specific combination of hardware circuitry and software, nor to any particular source for the instructions executed by the processing unit.

Memory 34 comprises a non-transient computer-readable medium storing transducer positioning search module 50, fetal heart window identification module 52, fetal heart monitoring module 54, signal quality compare module 56, pattern comparison module 58, cancellation comparison module 60 and data portion 62. Although memory 34 is illustrated as a single memory structure, in other implementations, different modules or different portions of data portion 62 may be stored at different memory locations. For example, some of items stored in memory 34 may be stored locally while other items may be stored remotely, accessible via a network.

Figure 2:
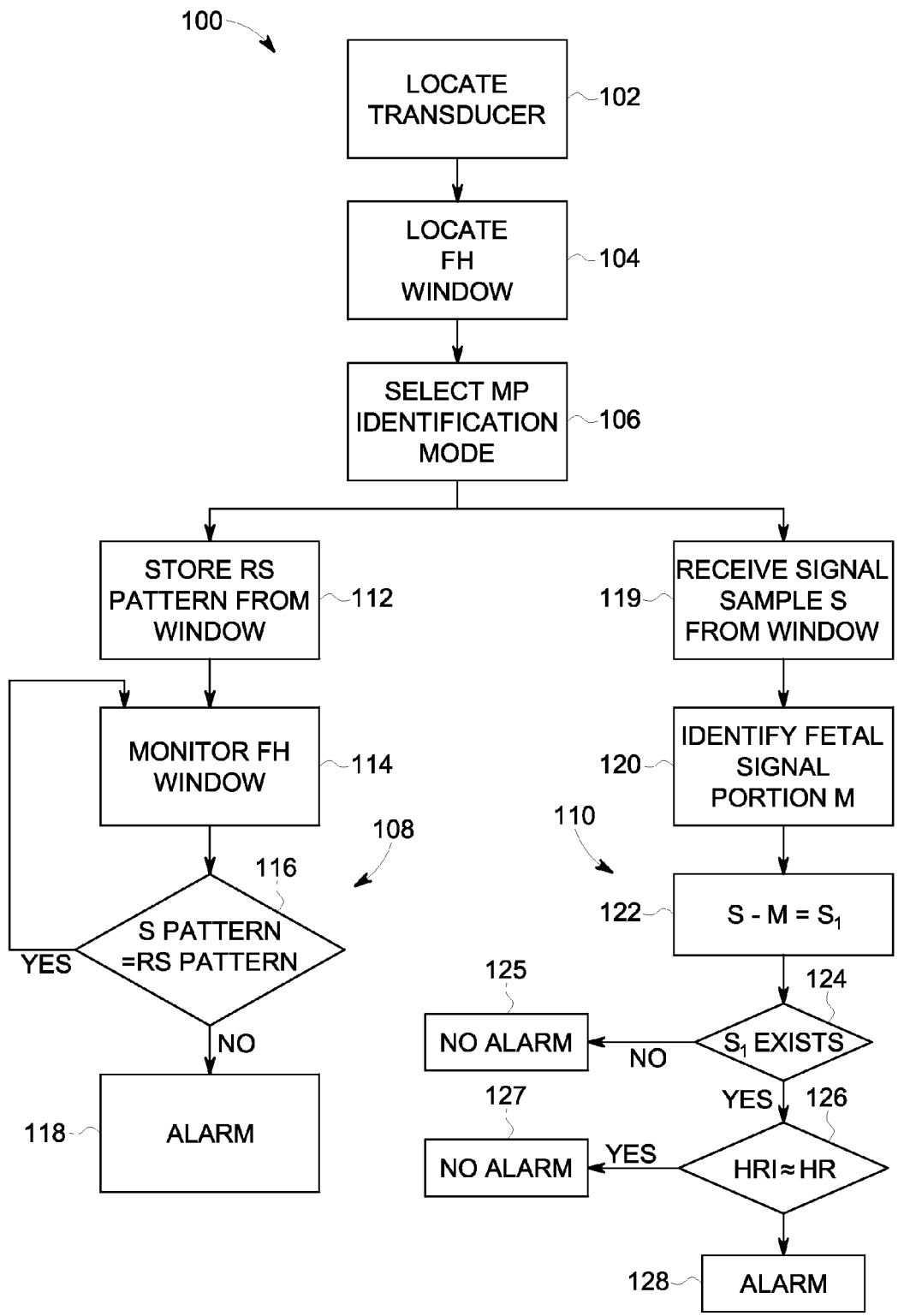
FIG. 2 is a flow diagram illustrating an example method for being carried out by the fetal heart monitoring system of FIG. 1.

Modules 50, 52, 54, 56, 58 and 60 each comprise a non-transient computer readable program or code stored in memory 34 and configured to direct processor 32 to carry out the process or method 100 shown in FIG. 2. As indicated by step 102, processor 32, following instructions contained in transducer positioning search module 50, directs or instructs processor 32 during a transducer position search mode. During this mode, transducer 24 is moved by caregiver, across abdomen 38 while emitting and receiving ultrasound signals to identify a location for transducer 24 upon abdomen 38 that produces the strongest signals reflected from the heart of fetus 22. In one implementation, during the transducer positioning search mode, processor 32 directs transducer 24 to transmit and receive ultrasound beams across a full range (nominally 3 cm to 30 cm) of transducer 24 as a caregiver manually repositions transducer 24 at different locations on abdomen 38. Processor 32 may direct display 28 or strip recorder 26 to provide a visual representation of the ultrasound signals received by transducer 24. Processor 32 may further amplify ultrasound signals and cause audible output corresponding to the heartbeats to be output by speaker 30. As a result, the caregiver may use the audible output to identify the location for transducer 24 on abdomen 28 where the output from speaker 30 is characteristic of a fetal heart beat and is the strongest or loudest.

As indicated by step 104 in FIG. 2, once transducer 24 has been properly located on abdomen 38, following instructions contained in fetal heart FH window identification module 52, processor 32 identifies and defines a window or volume containing the heart of fetus 42. In identifying the window, processor 32 utilizes received ultrasound signals to determine an approximate distance between ultrasound transducer 24 and the fetal heart. Based upon this approximate distance, processor 32 identifies a range or window containing the fetal heart and including a maximum and a minimum distance from transducer 24. In one implementation, processor 32 defines the range or window such that the boundaries of this range or window are spaced from the estimated perimeter of the fetal heart by a predetermined distance. As a result, the likelihood that the fetal heart will remain within the identified range or window, despite movement of fetus 22 or movement of the mother, is increased.

In one implementation, the boundaries of this range are spaced from the estimated perimeter of the fetal heart by at least 3 cm. In one implementation, the range has a 3 cm wide central portion larger than the 1 to 2 cm size of a fetal heart and 3 cm cushions to each side of the central portion. In other examples, the range or window may be spaced from the perimeter of the fetal heart by different distances.

In other examples, the range may comprise only one of a minimum distance or a maximum distance from transducer 24. In one implementation, the window is two-dimensional, contained in a sagital plane. In another implementation, the window defined by processor 32 may be three-dimensional, defining a volume about the fetal heart.

Figure 3:
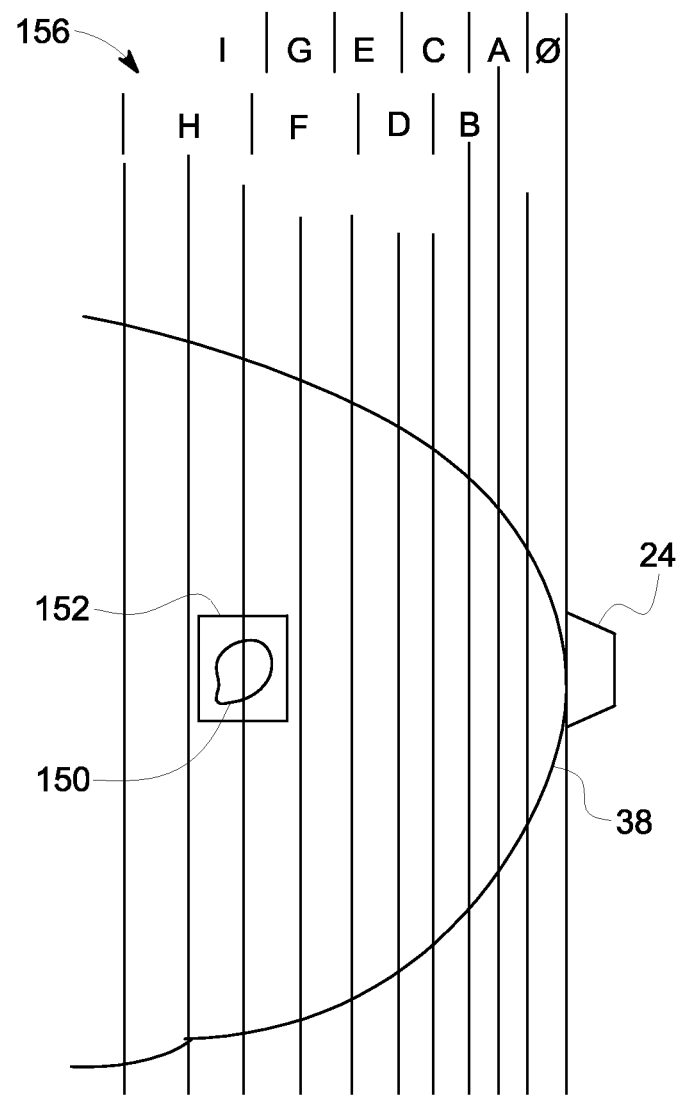
FIG. 3 is a diagram illustrating an example method for identifying a fetal heart window using signals from a transducer.
Figure 4:
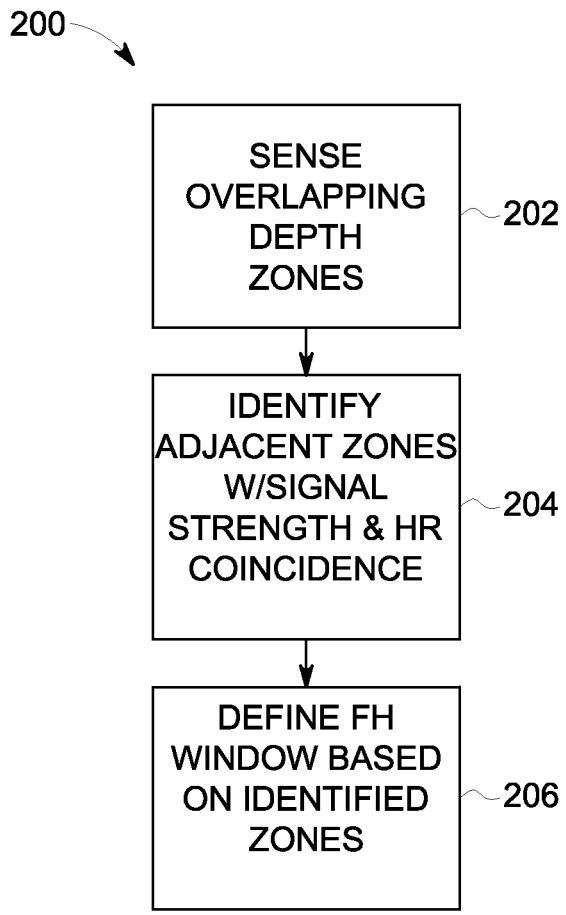
FIG. 4 is a flow diagram illustrating an example method for identifying a fetal heart window using signals from a transducer.

FIGS. 3 and 4 illustrate one method by which processor 32, following instructions provided by module 52, may identify a fetal heart window. FIG. 3 illustrates transducer 24 positioned against abdomen 38 and positioned for sensing a fetal heart rate of fetal heart 150. FIG. 4 is a flow diagram of a method 200 for identifying window 152 (shown FIG. 3) about fetal heart 150.

As indicated by step 202 in FIG. 4, when operating in a scanning mode, following instructions provided by module 52, processor 32 generates control signals causing transducer to sense overlapping abdominal depth zones 156 (labeled A-H in FIG. 3). In particular, processor 32 generates control signals causing transducer to emit ultrasound beams and receive reflected ultrasound signals at each of the depth zones. In one example, processor 32 causes transducer 24 to emit and receive signals from the following overlapping 6 cm depth zones: 3-9 cm, 6-12 cm, 9-15 cm, 12-18 cm, 15-21 cm, 18-24 cm, 21-27 cm and 24-30 cm. In other implementations, the width of each overlapping depth zone as well the degree to which such zones overlap one another may have other values or may vary from one zone to another zone. For example, at distances where the fetal heart is expected to be located, such zones may have smaller widths (the distance between the starting point and endpoint of the zone), resulting in a greater density of zones in the region expected to contain the fetal heart. In one implementation, the caretaker may choose the distribution of zones, impacting the density of zones going away from transducer 24. As a result, the precision at which the location of fetal heart 150 is identified may be enhanced.

In one implementation, processor 32 directs transducer 24 to scan through the entire range of abdominal depth zones 156. In another implementation, processor 32 prompts the caretaker to input (via a user input) the estimated depth the fetal heart 150 (the distance from transducer 24) or other physiological information regarding the mother, such as the mother's weight, height, and the like or information regarding the fetus such as the fetus's age, weight, orientation and the like or information pertaining to the stage of birthing, wherein processor 32 uses such information to estimate the location of fetal heart 150. Based upon the estimated location of fetal heart 150, processor 32 eliminates outlier zones 156, scanning only those zones 156 more likely to contain fetal heart 150. As a result, the location of fetal heart 150 may be located more quickly.

Upon receiving ultrasound signals from transducer 24 in each zone 156, processor 32 evaluates or measures two characteristics: a strength of the ultrasound signal from the particular zone and a degree of coincidence between the heart rate from a particular zone and a detected heart rate from a collection of zones. In one implementation, processor 32 generate control signals causing transducer 24 to emit and receive ultrasound beams across multiple zones 156 or across all of the zones 156 at the same time or in close proximity to the time at which each individual zone is sensed. For example, in one implementation using a single transducer 24, processor 32 may utilize the single transducer 24 to alternately sense (A) all the zones 156 or the entire abdominal area (3 cm-30 cm in the above example) and (B) the individual zones 156

(using time division multiple access (TDMA)). In such an implementation processor 32 also evaluates the coincidence or the degree to which the heart rate in an individual zone 156 coincides with or matches the heart rate sensed from the collection of zones or entire the abdomen area (3-30 cm in the above example).

As indicated by step 204 in FIG. 4, upon sensing and collecting the signal strength and heart rate coincidence from each zone 156, processor 32 identifies a pair of adjacent zones 156 having the greatest signal strength and the highest heart rate coincidence. For example, in some circumstances, two sets of adjacent zones may exhibit relatively strong ultrasound signals. In such a circumstance, processor 32 compares the heart rate of the signals occurring in each of the two sets of adjacent zones to the heart rate of ultrasound signals received from the entire range (3 cm to 30 cm in the above example). The pair of adjacent zones having ultrasound echo signals having the highest degree of coincidence of heart rate with the heart rate of echo signals from the entire range is identified by processor 32 as the set of adjacent zones that should serve as a basis for the window 152.

As indicated by step 206 in FIG. 3, processor 32 utilizes the distance boundaries of the selected two adjacent zones for defining the fetal heart window 152. In one implementation, processor 32 identifies the overlapping portion of the two adjacent zones as a central portion of the window 152. It is this central portion of the window that necessarily contains the entirety of the fetal heart. For example, if the zones having the highest strength and degree of heart rate coincidence are zones 9-15 cm and 12-18 cm, the overlapping portion of such zones occurs at a depth of 12 cm to 15 cm. It is this overlapping portion that necessarily contains a fetal heart.

Using this information, processor 32 then forms a window that includes a spacing or cushion. Processor 32 defines the window 152 as having proximal and distal boundaries (with respect to transducer 24) that are plus-minus a predefined distance from the overlapping portions of the adjacent zones. In the example illustrated, processor 32 utilizes the proximal and distal boundaries of the two overlapping zones as the inner and outer boundaries of the window 152, thus providing window 152 with a spacing or cushion on either side of the overlapping portion of the zones. For example, a window based upon overlapping zones of 9 to 15 cm and 12 to 18 cm would have a proximal boundary of 9 cm and a distal boundary of 18 cm, with the fetal heart being located within the overlapping portion of 12 to 15 cm. Once defined, the location of fetal heart 150 and the boundaries of window 152 are stored by processor 32 in a window location (WL) portion 66 of data storage portion 62 in memory 34. In other implementations, other distances or other cushions may be used to establish the inner and outer boundaries of window 152.

Although method 200 identifies adjacent zones and defines the fetal heart window 152 based upon both signal strength and heart rate coincidence, in other implementations, only one of these factors may be utilized to identify the adjacent zones 156 used as a basis for defining window 152. In other implementations, additional sensed factors or input criteria may be used to identify the adjacent zones 156 used as a basis for defining window 152. In still other implementations, such as where the density of zones in a region is higher (the width of the zones the smaller), processor 32 may utilize more than two zones for estimating the location of fetal heart 150 and for defining window 152.

Upon defining window 152, as indicated by step 106 in FIG. 2, processor 32 prompts a caretaker to input or select from one of two available maternal pulse (MP) identification modes 108 and 110. As will be described hereafter, mode 108 periodically compares a degree of correlation between a monitored pattern of an ultrasound echo signal with an initially stored reference pattern of an ultrasound echo signal to identify the presence or influence of maternal pulse. In one implementation, a reference spectrum of the stored ultrasound echo signal is compared with a spectrum of the monitored ultrasound echo signal.

In contrast, mode 110 determines the presence of any maternal pulse within the initially located window 152 by mathematically canceling a fetal heart signal from a composite monitored signal. If the signal remaining after the cancellation is determined to include a maternal pulse, the caretaker is notified and the transducer is repositioned. In one implementation, this process is repeated until the presence of a maternal pulse in the window 152 is no longer being detected. Once the transducer 24 is positioned such that the window 152 exhibits no maternal pulse, monitoring proceeds without subsequent testing for maternal contribution to the signal since a maternal aorta is not subject to movement like a fetal heart. However, the transducer 24 may be repositioned as a result of a poor or weak signal resulting from fetal movement. Such repositioning of transducer 24 may justify identifying a new fetal heart window 152 and once again carrying out the method of mode 110 to ensure that the new fetal heart window does not cover the maternal abdominal vessels that line the abdominal aorta and influence the ultrasound results. In other implementations, fetal heart monitoring system 20 may offer only one of the two correlation or cancellation modes 108 and 110, respectively.

As indicated by step 112, if mode 108 is selected, processor 32 stores an initial pattern of a reference ultrasound echo signal received from the selected window 152. In one implementation, the pattern of the reference ultrasound echo signal (i.e., reference pattern) is stored by processor 32 in reference pattern RP storage portion 68 of data storage portion 62 of memory 34 (shown in FIG. 1). As indicated by step 114, once the pattern of the reference ultrasound echo signal is stored, following instructions provided by fetal heart monitoring module 54, processor 32 generates control signals directing transducer 24 to emit and receive ultrasound signals focused at the fetal heart window 152 shown in FIG. 3.

As indicated by step 116, as processor 32 receives the signals from transducer 24 representing the reflected ultrasound signals (the "monitored signals" S), following instructions contained in pattern comparison module 58, processor 32 evaluates the pattern of the monitored signals by comparing the pattern of the monitored signals with the pattern RS of the reference signals stored in reference pattern storage portion 68. If the pattern of the monitored signals sufficiently correlates to pattern of the reference signals, no alarm is output and the monitoring of the fetal heart window 152 continues. However, as indicated by step 118, if the pattern of the monitored signals does not sufficiently correlate to the corresponding pattern of the reference signals, processor 32 determines that at least part of the signal received from transducer 24 may be a result of transducer 24 sensing blood flow (the maternal pulse) through the maternal abdominal vessels. As result, processor 32 generates control signals causing an alarm to be presented to the caretaker using at least one of outputs 26, 28 and 30. In one implementation, an audible alarm is generated by speaker 30 in response to such control signals from processor 32 indicating a condition where the ultrasound signals being received from transducer 24, being displayed on display 28 and being imprinted by strip recorder 26 may be at least partially influenced by maternal abdominal vessels. Upon being alerted to such a condition, a caretaker may take remedial action such as repositioning or adjusting the location of transducer 24 or the abdominal depth at which transducer 24 is sensing. The caretaker may also verify the condition or health of fetus 42 (shown FIG. 1).

In one implementation, to determine if the pattern of the monitored signals sufficiently corresponds to the pattern of the reference signals, processor 32 evaluates the comparison against a predefined matching threshold stored in correlation threshold TH portion 70 of data storage portion 62 of memory 34 (shown in FIG. 1). The threshold has a value selected such that the threshold is low enough to be exceeded despite changes in the monitored ultrasound echo signals merely due to fetal heart angular orientation changes, avoiding false alarms. At the same time, the threshold has a value that is high enough so as to not be exceeded when changes in the monitored ultrasound echo signals are due to worsening fetal conditions or due to the influence maternal or fetal movements that cause the transducer 24 to undesirably lock onto unwanted maternal abdominal vessels.

In one example, an averaged amplitude spectrum of the fetal heartbeat is used as a pattern of the reference signals against which an averaged amplitude spectrum of the monitored signal is compared. In one implementation, a correlation coefficient is utilized as a measure of similarity between the patterns of monitored signals and the reference signal. In one example, an averaged amplitude spectrum is obtained from the monitored signals at each 10 second interval with a sampling rate of 2 ksps. The correlation coefficient is a Pearson coefficient of correlation between reference signal and monitored signal. If the coefficient is below the threshold, a caretaker is notified or presented with an alarm indicating the loss of a fetal heart signal and possible lock on maternal abdominal vessels. In other examples, the correlation or matching between the reference signals and the monitored signals may be made using other patterns, other sampling rates and other correlation coefficients.

As indicated by step 119, if the cancellation mode 110 is selected, following instructions provided by fetal heart monitoring module 54, processor 32 generates control signals directing transducer 24 to emit and receive ultrasound signals focused upon the fetal heart window 152 shown in FIG. 2. In one implementation, a sample of ultrasound echo signals is received for a predefined period of time. In one implementation, ultrasound echo signals received for predefined period 10 seconds. Following instructions contained in cancellation comparison module 60, processor 32 then utilizes this sample of ultrasound echo signals to determine the presence of a maternal pulse within the fetal heart window 152 in steps 120-126.

As indicated by step 120, processor 32 identifies a fetal signal portion M (fetal heart signal contribution) of the sample ultrasound echo signal received during the predefined time period. A fetal heart signal contribution is a component of an ultrasound Doppler echo signal that is caused by pulsations of a fetal heart. As indicated by step 122, processor 32 then subtracts the identified fetal signal portion M from the composite monitored ultrasound echo signal. The remaining portion of the ultrasound echo signal S1 is then used by processor 32 to determine whether a maternal pulse (maternal contribution, if any) is being detected in window 152 with the current positioning of transducer 24 upon abdomen 38 (shown in FIG. 1). A maternal contribution is a component of an ultrasound Doppler echo signal that is caused by pulsations of blood in maternal abdominal muscles.

As indicated by step 124, following instructions contained in cancellation comparison module 60, processor 32 evaluates the left over or remaining signal or value S1. If there is no remaining quasi-periodic signal S1, no alarm is provided as indicated by step 125 such that continuous monitoring of the fetal heart may begin. Alternatively, as indicated by step 126, if there is a remaining quasi-periodic signal S1, processor 32 compares the heart rate HR1 obtained or detected on remaining signal S1 to the initial heart rate HR (the heart rate calculated on the composite monitored ultrasound echo signal prior to cancellation) to determine if the heart rate of remaining signal S1 coincides with the initial heart rate HR (i.e., heart rate obtained on composite monitored echo signal). If the heart rate HR1 of the remaining signal S1 coincides with the initial heart rate HR, no alarm is provided as indicated by step 127 such that continuous monitoring of the fetal heart may begin.

However, as indicated by step 128, if the heart rate HR1 of the remaining signal S1 does not satisfy a predetermined degree or threshold of coincidence with the initial heart rate HR, processor 32 determines that at least part of the signal received from transducer 24 is a result of transducer 24 sensing blood flow (the maternal pulse) through the maternal abdominal vessels. As result, processor 32 generates control signals causing an alarm to be presented to the caretaker using at least one of outputs 26, 28 and 30. In one implementation, an audible alarm is generated by speaker 30 in response to such control signals from processor 32 indicating a condition where the ultrasound signals being received from transducer 24, being displayed on display 28 and being imprinted by strip recorder 26 may be at least partially influenced by maternal abdominal vessels. Upon being alerted to such a condition, a caretaker may take remedial action such as repositioning or adjusting the location of transducer 24 or the abdominal depth at which transducer 24 is sensing. The caretaker may also verify the condition or health of fetus 42 (shown FIG. 1).

Figure 5:
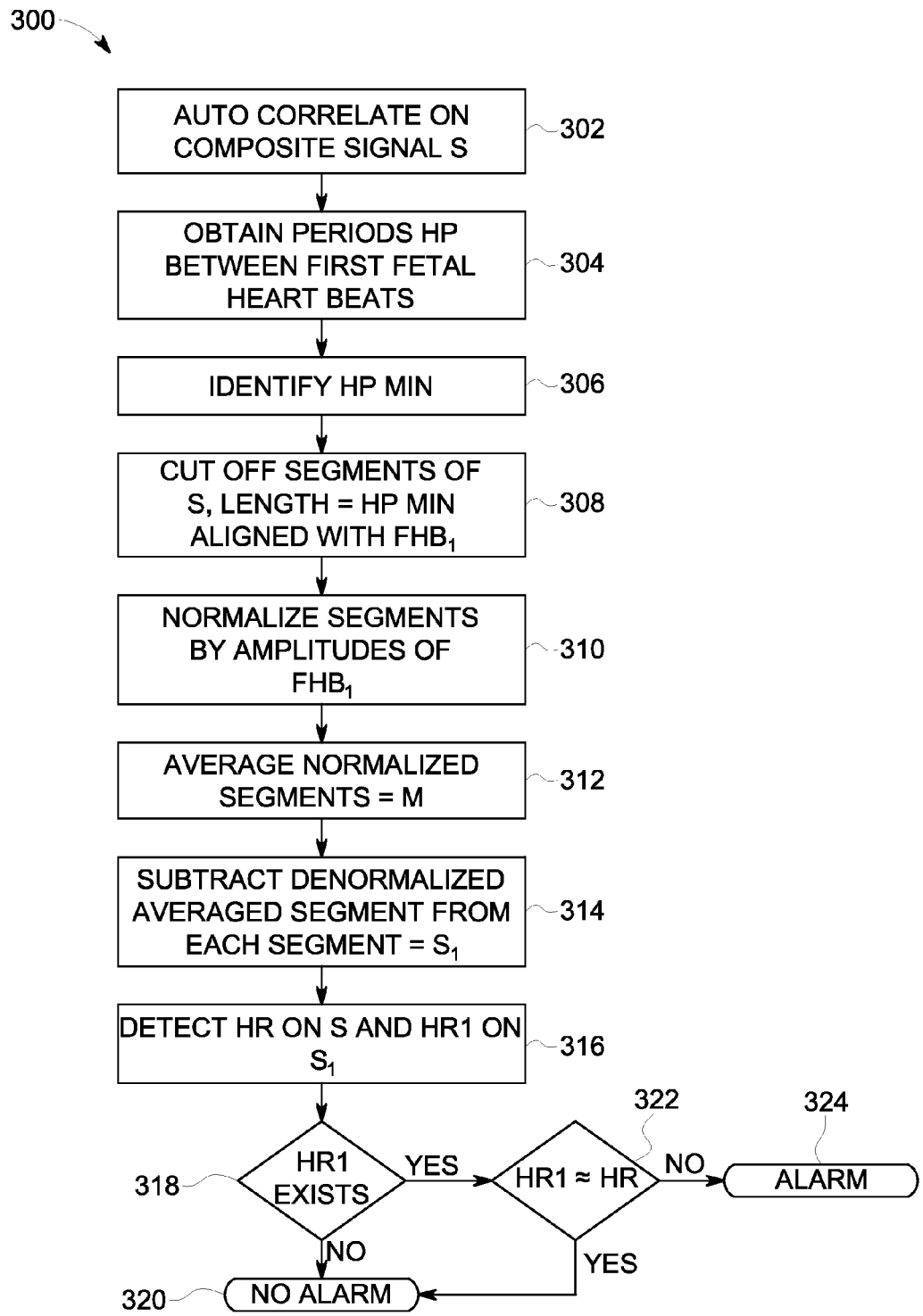
FIG. 5 is a flow diagram illustrating an example cancellation method for identifying the presence of a maternal signal.
Figure 6:
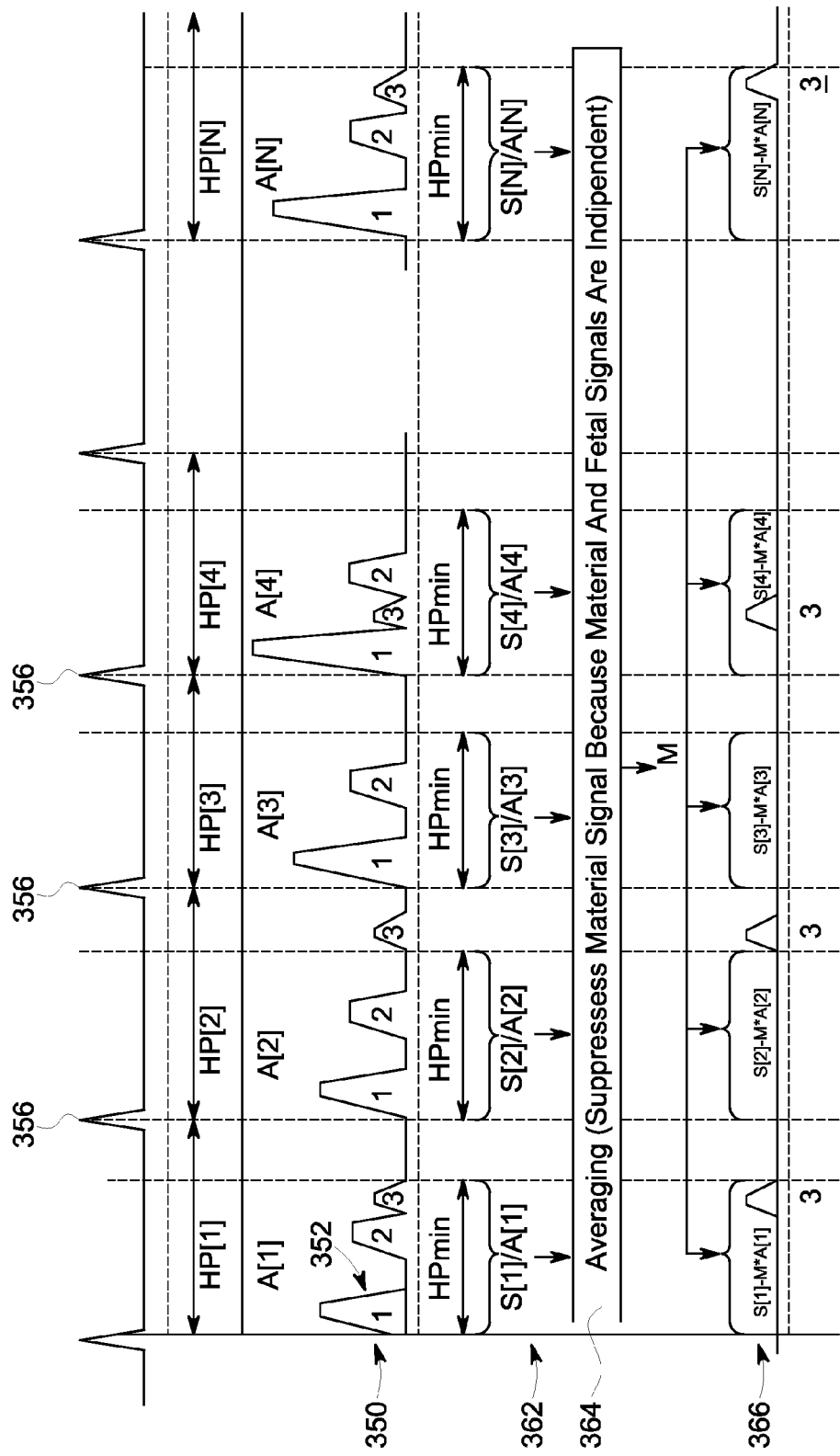
FIG. 6 is a data flow diagram illustrating an example data flow during the method of FIG. 5.

FIG. 5 illustrates method 300, one example implementation of mode 110. FIG. 6 illustrates one example data flow diagram for method 300. As noted above, pursuant to step 119, in one implementation, a sample ultrasound echo signal S is received for a period of 10 seconds. An example ultrasound echo signal S 350 taken from window 152 (shown in FIG. 3) is shown in FIG. 6. As shown by FIG. 6, signal S 350 includes multiple fetal set of heartbeats 352, each set 352 including a first beat 1 and a second beat 2. The sample signal S 350 may further include maternal signals 3.

Steps 302-312 serve to identify a fetal signal portion M from the composite ultrasound echo signals 350 by suppressing any maternal contribution from the original or raw signal S 350. As indicated by step 302, processor 32 performs autocorrelation on the signal S 350 to produce the fetal heart beat peaks 356 (based upon the first fetal heartbeat) shown in FIG. 6. As indicated by step 304, processor 32 determines or obtains the periods between such fetal heart beat peaks. As shown by FIG. 6, the distance between adjacent peaks 356 constitute periods HP[n] where n=1 . . . N. As indicated by step 306 in FIG. 5, using the calculated periods, processor 32 identifies the minimum fetal heartbeat period HPmin. As indicated by step 308 in FIG. 5, processor 32 uses this determined HPmin to cut off segments in the signal S 350. In the example illustrated, such segments have a length of HPmin and are lined with the first fetal heartbeat (FHB$_1$) of each set of heartbeats 352. Example a composite signal segments S[n] where n=1 . . . N are shown in FIG. 6.

As indicated by step 310, for each composite signal segment S[n] starting at an auto correlation peak 356 and having a duration of HPmin, processor 32 normalizes the segment by dividing it by amplitude A[n] of first beat of fetal signal in the associated segment S[n] as shown by data flow portion 362. As indicated by step 312 and indicated by block 364 in FIG. 6, processor 32 determines an average of the normalized segment signals S[n], n=1 ... N. This average constitutes a normalized model M of the fetal signal (the fetal heart signal contribution).

As indicated by step 314, to determine maternal signal contribution, the fetal heart signal contribution (model M) is then canceled from the original raw signal S, wherein the results of this cancellation are used to determine whether an alarm should be outputted. In the example illustrated, as indicated by step 314, processor 32 subtracts a denormalized model M from each composite segment S[n] to identify remaining signal S1[n]. In particular, as shown dataflow line 366 by FIG. 6, the model M is denormalized for each segment S[n] by multiplying the model M by the amplitude A[n] of the first beat of the fetal signal in the associated segment S[n]. In the example shown in FIG. 6, such subtraction results in possible presence of maternal pulse signal 3 (online 366 in FIG. 6) in remaining signal S1[n] 366.

As indicated by step 316, processor 32 also detects heart rate HR (which is the fetal heart rate) on signal S and heart rate HR1 on signal 51 which is a composite signal after fetal signal cancellation. The fetal heart rate HR is in beats per minute as defined by formula HR[n]=60,000/HP[n], n=1 ... N where HP[n] are distances in microseconds between correlation peaks on line 356 of FIG. 6. The heart rate HR1 of signal S1 remaining after fetal signal cancellation is defined by formula HR1[i]=60,000/HP1[i], i=1 ... I, where HP[i] are distances in milliseconds between correlation peaks of autocorrelation function (not shown) of S1 shown on line 366 of FIG. 6.

As indicated by step 318, processor 32 determines whether any heart rate HR1 of remaining signal S1 exists after such subtraction. If no heart rate HR1 of remaining signal S1 exists, no alarm is provided as indicated by step 320. Alternatively, if there is a heart rate HR1 of remaining signal S1, processor 32 determines whether the heart rate HR1 of remaining signal coincides with the fetal heart rate HR obtained on signal S. As indicated by step 322, if the heart rate HR1 of remaining signal S1 satisfies a predetermined or predefined degree of coincidence with the fetal heart rate HR of fetal signal, no alarm is provided as indicated by step 324. Alternatively, if the heart rate HR1 of remaining signal S1 does not coincide with the fetal heart rate HR, processor 32 causes an alarm to be generated as indicated by step 320. In one implementation, the predetermined degree of coincidence is established by a threshold of 5 beats per minute, wherein if HR1 and HR are different by more than this threshold, the alarm in step 324 is outputted. In other implementations, other predetermined degrees of coincidence or other thresholds may be utilized.

As noted above, processor 32 generates control signals causing an alarm to be presented to the caretaker using at least one of outputs 26, 28 and 30. In one implementation, an audible alarm is generated by speaker 30 in response to such control signals from processor 32 indicating a condition where the ultrasound signals being received from transducer 24, being displayed on display 28 and being imprinted by strip recorder 26 may be at least partially influenced by maternal abdominal vessels. Upon being alerted to such a condition, a caretaker may take remedial action such as repositioning or adjusting the location of transducer 24 or the abdominal depth at which transducer 24 is sensing. Once the transducer has been repositioned, method 300 may be performed once again. This process may be repeated until such repositioning results in no alarm being provided, indicating that the positioning of transducer 24 upon abdomen 38 is such that the window 152 is not influenced by any maternal pulse. At this point time, normal continuous monitoring of the fetal heart rate may be carried out by fetal heart monitoring system 20.

Figure 7:
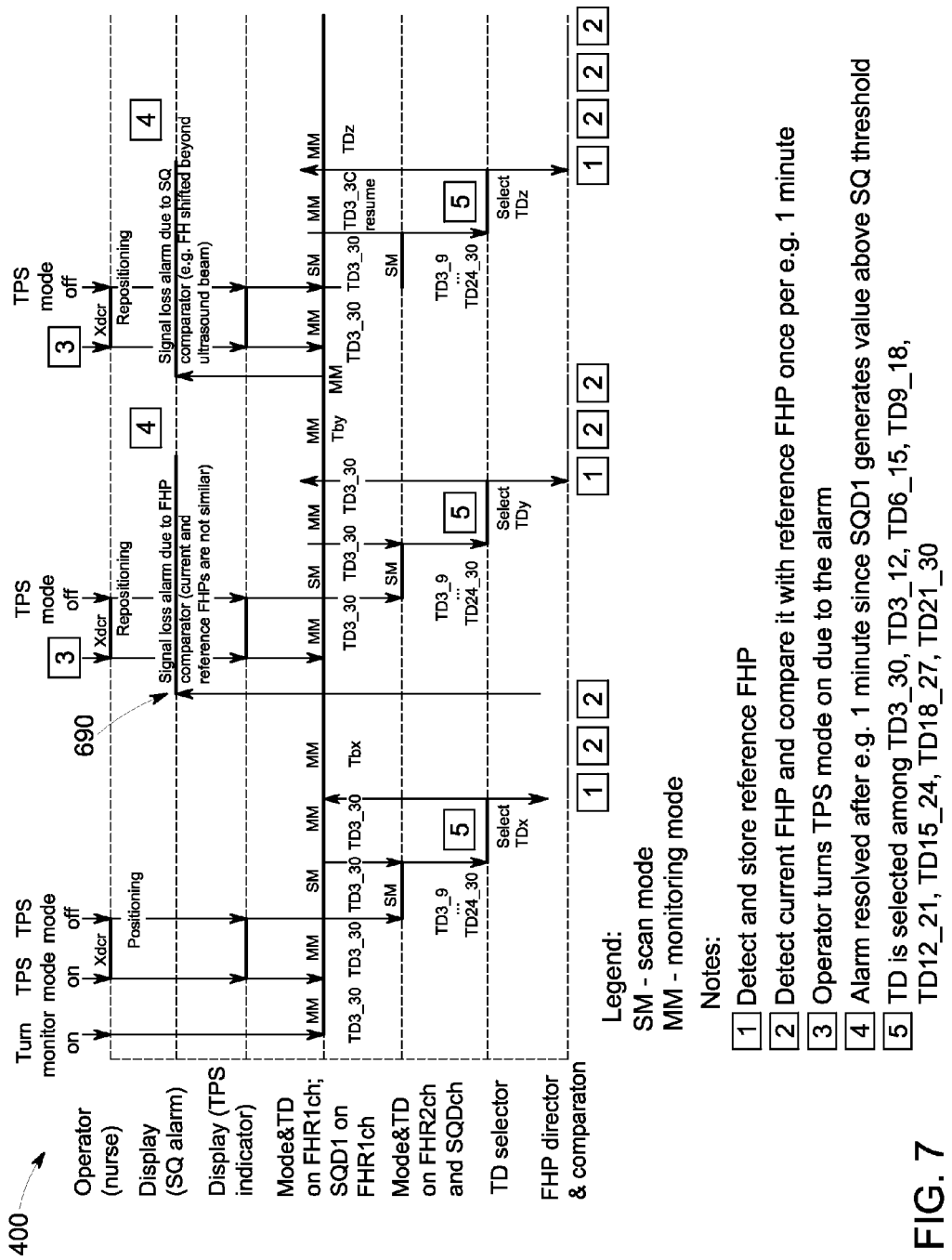
FIG. 7 is a control flow diagram of an example method for fetal heart monitoring using a correlation mode to identify the influence of maternal signals.
Figure 8:
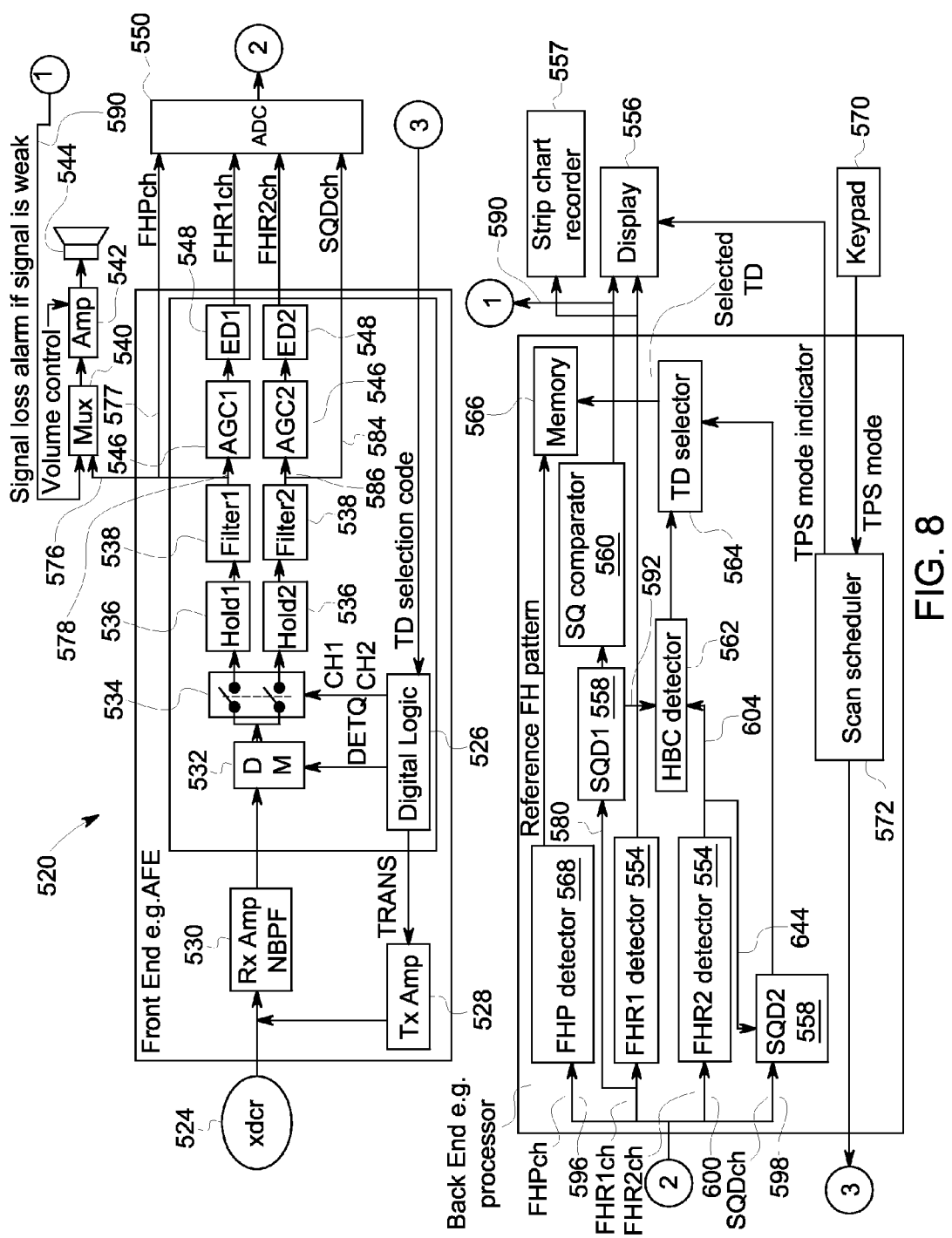
FIG. 8 is a diagram schematically illustrating an example implementation of the fetal heart monitoring system of FIG. 1 for carrying out the method of FIG. 7.

FIG. 7 is a control flow diagram illustrating an example method 400 for monitoring a single fetus. FIG. 8 is a block diagram schematically illustrating portions of an example fetal heart monitoring system 520, one implementation of fetal heart monitoring system 20, that may be used to carry out portions of method 400. FIG. 8 illustrates those components of system 520 which are utilized to define or identify a fetal heart window, such as the fetal heart window 152 shown in FIG. 3. FIG. 8 further illustrates components of system 520 which are utilized to initially position transducer 24 upon abdomen 38. As shown by FIG. 8, fetal heart monitoring system 520 comprises transducer 524 and analog components: digital logic 526, transmit signal amplifier 528, receive echo amplifier and narrow band filter 530 (center frequency about 1 MHz, for example), demodulator 532, receives strobe pulse switch 534, sample and hold capacitors 1 and 2 (536), band pass filters 1 and 2 (538), multiplexer 540, amplifier 542, speaker 544, automatic gain controllers 1 and 2 (546), envelope detectors 1 and 2 (548) and analog-to-digital converter 550. In other implementations, such analog components may alternatively be provided by digital components or be implemented in software for the processor.

As further shown by FIG. 8, fetal heart monitoring system 520 also includes a backend system implemented in software. Such backend components comprise fetal heart rate detectors 1 and 2 (554), display 556, strip chart recorder or printer 557, signal quality detectors 1 and 2 (558), signal quality comparator 560, heart beat coincidence detector 562, window selector (also known as timing diagram (TD) selector) 564, memory 566, fetal heart pattern detector 568, keypad 570 and scan scheduler 572.

As shown by the control flow diagram of FIG. 7, the transducer 524 (shown in FIG. 8) is first located on the surface of the maternal abdomen. As shown in FIG. 7, the caretaker (operator or nurse) turns fetal heart monitoring system 520 on and inputs a command to scan scheduler 572 via keypad 570 (shown in FIG. 8) to enter a transducer position search mode. In response to this command, digital logic 526, comprising a field programmable gate array (FPGA), a complex programmable logic device (CPLD) or a processor, generates ultrasound transmit tone signals TRANS (nominally having a character frequency of approximately 1 MHz) which are amplified by amplifier 528 and directed by transducer 524 towards fetus 42 (shown in FIG. 1). In the example illustrated, during this search mode, transducer 524 senses an entire range of 3 cm to 30 cm as the caretaker repositions transducer 524 looking or listening through speaker 544 for the strongest echo signal having the characteristics of the fetal heart beat.

Echo signals, which correspond to the reflected pulses having a frequency corresponding to the speed of fetal heart contractions, are received by transducer 524 and are amplified by a receive echo amplifier 530. After being amplified, the echo signals undergo signal processing. In the implementation illustrated, the signals are demodulated by demodulator 532, transmitted across Channel 1 comprising: sample and hold capacitor HOLD 1 536, band pass filter 538 (Filter 1), automatic gain control AGC1 546 and envelope detector ED1 548. In the example illustrated, each of band pass filters 1 and 2 (538) filter out signals having a frequency below 100 Hz and above 300 Hz to remove extraneous signals. As indicated by arrow 576, the signal of filter 1 is transmitted to multiplexer 540 and is amplified by amplifier 542 for audible output via speaker 544.

As further indicated by arrow 578, the signal of filter 1 further passed through automatic gain controller 1 (546) which provides such signals with a stable amplitude, eliminating variability associated with different distances between fetal heart and the transducer 524. After such signals undergo envelope detection by envelope detector 1 (548), such signals are transmitted to analog-to-digital converter 550 for digital conversion for use by the backend digital componentry of fetal heart monitoring system 520. As noted above, in some implementations, such analog component premier place for digital componentry.

In the transducer positioning search mode, only one channel (channel 1) is utilized. Signals from the analog-to-digital converter are transmitted to fetal heart rate detector 1 (554) which identifies a fetal heart rate and outputs the estimated fetal heart rate to the display 556 and strip recorder 557. Using mostly the audible output from the speaker 544 as well as the visual output on either of display 556 or printer 557, the caretaker may continuously reposition transducer 24 upon abdomen 38 until the strongest signal characteristic of a fetal heartbeat is being heard on speaker 544 and/or seen on the output of display 556 and/or printer 557. Once the caretaker has positioned transducer 544 at the initial monitoring position against the abdomen, the caretaker inputs a command via keypad 570 exiting the transducer position search mode. As result, scan scheduler 572 causes monitoring system 520 to initiate a scanning mode SM (shown in FIG. 7), either automatically or in response to a command entered by the caretaker using keypad 570.

Figure 9:
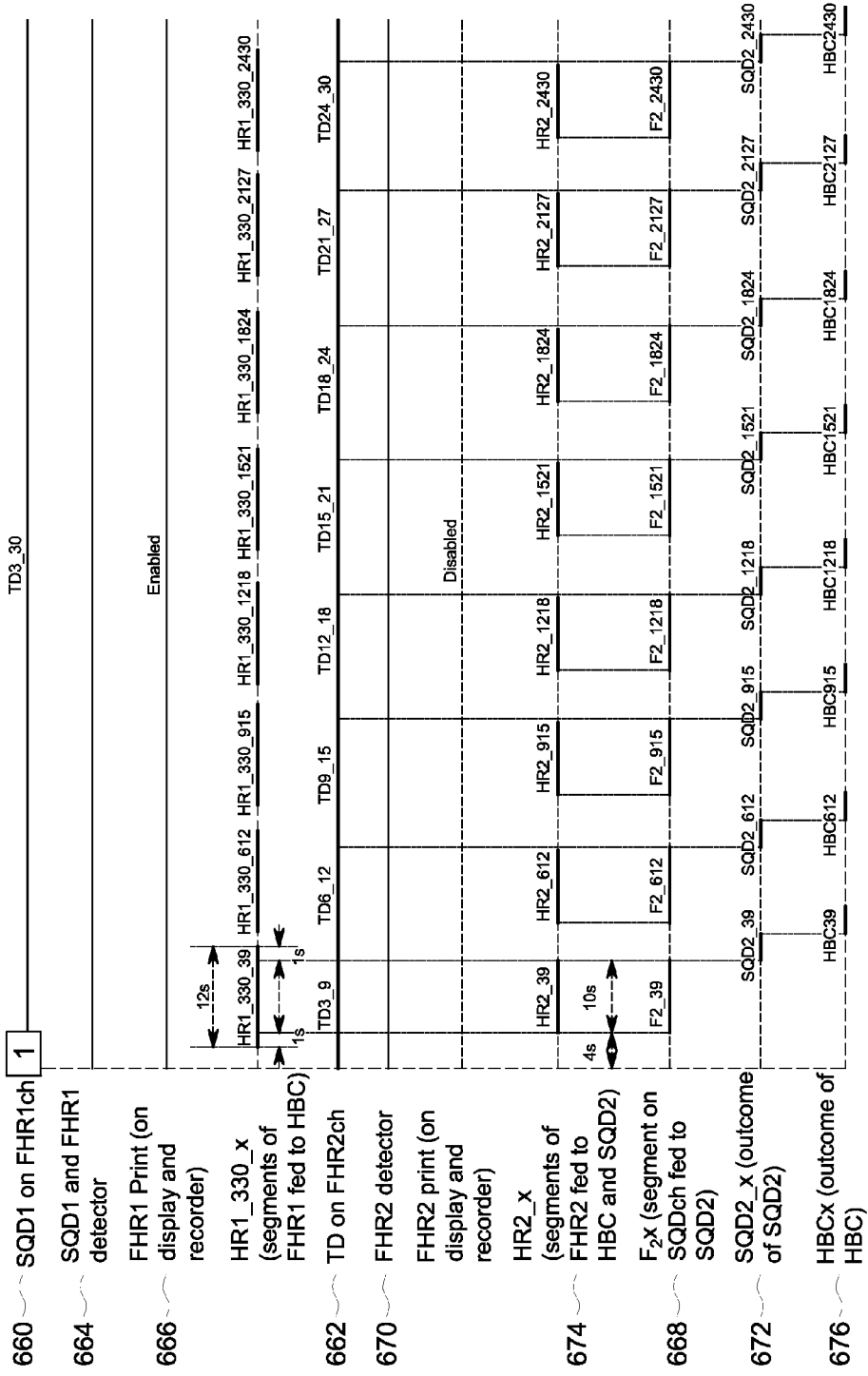
FIG. 9 is a control flow diagram of an example method of scanning to identify a fetal heart window.

In the scanning mode SM, method 200 (shown in FIG. 4) is carried out. FIG. 9 is a control flow diagram and an associated table illustrating the operation of system 520 during the scanning mode. As indicated by lines 660 and 662 in FIG. 9, in the particular fetal heart monitoring system example 520, digital logic 526 generates ultrasound transmit tone signals TRANS (nominally having a carrier frequency of approximately 1 MHz) which are amplified by amplifier 528 and directed by transducer 524 towards fetus 42 (shown in FIG. 1). In the example illustrated, during this scanning mode, digital logic 526 generates ultrasound transmit tone signals which are amplified by amplifier 528 such that transducer 524 alternately emits ultrasound signals and receives ultrasound echo signals from (A) an entire range of 3 cm to 30 cm (line 660 in FIG. 9) and (B) each of the depth zones (line 662 in FIG. 9).

In one example, digital logic 526 causes transducer 524 to emit ultrasound signals and receive echo signals from (A) an entire range of 3 to 30 cm and (B) the following overlapping 6 cm depth zones: 3-9 cm, 6-12 cm, 9-15 cm, 12-18 cm, 15-21 cm, 18-24 cm, 21-27 cm and 24-30 cm, in an alternating manner (time division multiple access (TDMA)) in a way that the echo signal from the entire range 3-30 cm is processed in channel 1 (Hold 1 to Filter 1 to AGC1 to ED1) while echo signals from current depth zone is processed in channel 2 (Hold 2 to Filter 2 to AGC2 to ED2).

Figure 9A:
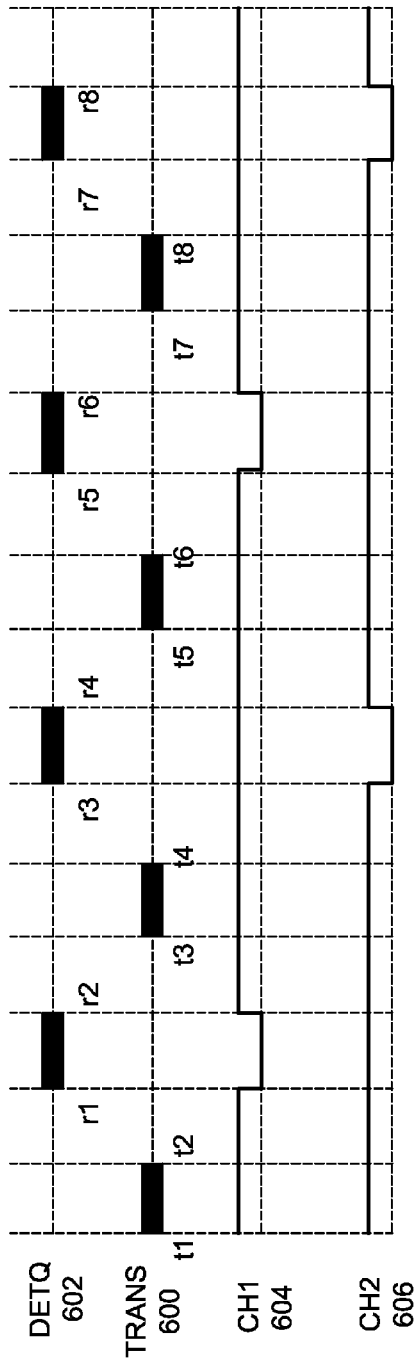
FIG. 9A is an example timing diagram illustrating the alternating transmission and receiving of ultrasound signals on different channels at different abdominal depths.

FIG. 9A is a timing diagram and associated timing tables illustrating one example of such alternating ultrasound penetration range scanning. As shown by FIG. 9, digital logic 526 and amplifier 528 cause transmit tone signals 600 to be emitted by transducer 524, wherein such emitted transmit tone signals 600 alternate between a tone directed at the entire range of 3 cm to 30 cm and a tone directed at one of the overlapping range subsets 3-9 cm, 6-12 cm, 9-15 cm, 12-18 cm, 15-21 cm, 18-24 cm, 21-27 cm and 24-30 cm. For example, during a first 12 seconds of the scan mode, each of tones t1-t2, t5-t6 and so on are directed at the entire range while tones t3-t4, t7-t8 and so on are directed at a range subset of 3 cm to 9 cm. Then during the next 12 seconds, each of tones t1-t2, t5-t6 and so on are directed at entire range while tones t3-t4, t7-t8 and so on are directed at range subset of 6-12 cm. Finally, during the last 12 seconds of scan mode each of tones t1-t2, t5-t6 and so on are directed at entire range while tones t3-t4, t7-t8 and so on are directed at range subset of 24-30 cm.

As shown by the demodulation tone signal line DETQ 602 in FIG. 9A, as well as by control signal lines CH1 604 and CH2 606 which alternatively connect demodulator 532 through switch 534 to either channel 1 or channel 2 of processing circuitry (or SW if frontend is implemented in SW), transducer 524 alternately receives echo signals in a similar fashion. For example, during first 12 seconds of scan mode transducer 524 receives echo signals from the entire range within intervals r1-r2, r5-r6 while receiving echo signals from the range subset of 3-9 cm within intervals r3-r4, r7-r8 and so on. Then during the next 12 seconds of scan mode, transducer 524 receives echo signal from the entire range within intervals r1-r2, r5-r6 and so on while receiving echo signal from the range subset of 6-12 cm within intervals r3-r4, r7-r8 and so on. Finally, during the last 12 seconds of the scan mode, transducer 524 receives an echo signal from the entire range within intervals r1-r2, r5-r6 and so on while receiving echo signal from range subset of 24-30 cm within intervals r3-r4, r7-r8 and so on. The received echo signals are amplified by amplifier 530 and demodulated by demodulator 532. As shown by Channel 1 line 604 and channel 2 line 606 in FIG. 9A, such received echo signals are processed across channel 1 and channel 2 with channel 1 processing echo signals directed at the entire range and channel 2 processing echo signals directed at the overlapping ranges (3-9 cm, 6-12 cm and so on, wherein the ranges change at cycles (e.g., a 12-second duration for each cycle)).

Each of the signals transmitted across channels 1 and 2 on cyclical basis through range subsets, respectively, undergo signal processing. In the example implementation illustrated, each signal transmitted across channel 1 and corresponding to the entire depth range stored by sample and hold capacitor hold 1 536 and filtered by band pass filter 538 (Filter 1). In the example illustrated, the band pass Filter 1 filters out signals having a frequency below 100 Hz and above 300 Hz to remove extraneous noise. As indicated by arrow 576, these filtered signals are transmitted to multiplexer 540 and are amplified by amplifier 542 for audible output via speaker 544. As indicated by arrow 577, these filtered signals are directly transmitted through a separate fetal heart pattern channel (FHPch) to analog-to-digital converter 550 for subsequent transmission to fetal heart pattern detector 568.

As further indicated by arrow 578, the filtered signals are further passed through automatic gain controller 1 (546) which provides such signals with a stable amplitude, eliminating variability. After such signals undergo envelope detection by envelope detector 1 (548), such signals are transmitted to analog-to-digital converter 550 for digital conversion for use by the backend digital componentry of fetal heart monitoring system 520. As noted above, in some implementations, such analog components may be replaced with digital componentry or software.

Signals transmitted across channel 2 and corresponding to cycled through depth range subsets undergo signal processing in a similar fashion. In particular, such signals transmitted across channel 2 are stored by sample and hold capacitor 2 hold 2 536 and filtered by band pass filter 538 (Filter 2). In the example illustrated, the bandpass Filter 2 filters out signals having a frequency below 100 Hz and above 300 Hz to remove extraneous noise. As indicated by arrow 584, these filtered signals are directly transmitted through a separate signal quality detector channel (SQDch) to analog-to-digital converter 550 for subsequent transmission to signal quality detector 2 (558).

As further indicated by arrow 586, the filtered signals 2 are further passed through automatic gain controller 2 (546) which provides such signals with a stable amplitude, eliminating variability. After such signals undergo envelope detection by envelope detector 2 (548), such signals are transmitted to analog-to-digital converter 550 for digital conversion for use by the backend digital componentry of fetal heart monitoring system 520. As noted above, in some implementations, the functions of such analog componentry may alternatively be carried out or performed by software or digital componentry.

As shown by the bottom half of FIG. 8 and indicated by lines 664 in FIG. 9, signals from fetal heart rate channel 1 (FHR1ch) are transmitted from analog-to-digital converter 550 to fetal heart rate detector FHR1 (554) and SQD1 558. Fetal heart rate detector FHR1 (554) detects the fetal heart rate from such signals and outputs the detected fetal heart rate to display 556 and strip recorder 557 as indicated by line 666 in FIG. 9.

Signal quality detector 1 (558) detects the signal quality. As indicated by arrow 588, the detected signal quality is transmitted to signal quality comparator 560 which performs real-time evaluation of the power of the signal by comparing the power to a predetermined threshold. The signal quality measure is transmitted to display 556. As indicated by arrow 590, if signal quality is poor (as determined by the value with respect to the predetermined threshold), a signal loss alarm is transmitted to multiplexer 540, whereby an audible alarm is transmitted using amplifier 542 and speaker 544. As indicated by arrow 592, signals from FHR1 detector 554 are further transmitted to heartbeat coincidence detector 562.

As indicated by arrow 596, signals originating from Filter 1 538 are transmitted across the fetal heart pattern channel (FHPch) to fetal heart pattern detector 568 which stores the detected fetal heart pattern as reference FH pattern in memory 566. This reference FH pattern is subsequently used in determining pattern correlation.

As indicated by arrow 598 in FIG. 8 and line 668 in FIG. 9, signals originating across Filter 2 538 are transmitted across signal quality detection channel (SQDch) to signal quality detector 2 (558) which measures or evaluates the quality (strength etc.) of such signals. The results of the evaluation are transmitted to depth or zone selector 564 (referred also to as TD (timing diagram) selector for use in selecting a depth range subset for subsequent fetal heart monitoring.

As indicated by arrow 600 in FIG. 8 and line 670 in FIG. 9, signals originating from ED2 548 are further transmitted across fetal heart rate 2 channel (FHR2ch) to fetal heart rate 2 detector (554). Fetal heart rate 2 detector (554) detects the fetal heart rate for each of the particular depth sub ranges or subsets. As indicated by line 674 in FIG. 9, the detected fetal heart rate is transmitted to: (1) signal quality detector 2 (558) for use in the evaluation of the signal quality from the particular depth range or subset; and (2) HBC detector 562 for use in the evaluation of coincidence between fetal heart rate in channel 1 and heart rate in channel 2.

As indicated by line 672 in FIG. 9, signal quality detector 2 evaluates the signal quality. In one example, signal quality detector 2 evaluates the signal quality as follows:
1) Evaluation of power SPx of segments of signal on SQDch. Segments are aligned with segments HR2_$x$ (the detected fetal heart rate for a particular depth range subset).
2) SQD2_$x$=SPx*g(TDx) where x=39, 612, 915, 1218, 1521, 1824, 2127, 2430 (39 is an abbreviation of 3 cm to 9 cm, 612 is an abbreviation of 6 cm to 12 cm and so on) and g(TDx) is defined by Table 1 below to compensate acoustic attenuation.

TABLE 1

| TDx | g(TDx) |
|---|---|
| TD3_9 | 2 |
| TD6_12 | 2.8 |
| TD9_15 | 4 |
| TD12_18 | 5.6 |
| TD15_21 | 8 |
| TD18_24 | 11.2 |
| TD21_27 | 16 |
| TD24_30 | 22.4 |

In another implementation, signal quality detector 2 (558) evaluates a signal quality as follows:
1) y[i]=absolute_value(F2_$x$[i]), i=0 . . . I−1
   where:
   a) x=39, 612, 915, 1218, 1521, 1824, 2127, 2430
   b) I=10[s]*Fs
   c) Fs–sample rate (e.g. 1 ksps) of ADC
   d) 10[s]–length of segment F2_$x$
2) z[i]=sum (y[i+j], j=0 . . . 89)/90, i=0 . . . I−1−89
3) Zmax=max (z[i], i=0 . . . I−90)
4) z[i]=0 for i=Imax−BI, Imax−BI+1, . . . , Imax, Imax+1, . . . , Imax+BI−1, Imax+BI
   where:
   a) Imax–index of element Zmax in vector z[ ]
   b) BI=integer (60000/(HR2_$x$_mean+2*HR2_$x$_std))
   c) HR2_$x$_mean=mean (HR2_$x$[j], j=0 . . . 40−1)
   d) 40[sample]=10[s]*4[sample/s]
   e) 10[s]–length of segment HR2_$x$
   f) 4[sample/s]–conventional FHR output sample rate
   g) HR2_$x$_std=standard_deviation (HR2_$x$[j], j=0 . . . 40−1)
5) Put Zmax to Zmax_vector
6) If z[i]=0 for any i=0 . . . I−90 then go to step 7 else go to step 3
7) Get maximum element in vector Zmax_vector and zero it
8) Zmax_mean=mean (Zmax_vector)
9) SQD2_$x$=Zmax_mean*g(TDx) where g( ) is defined above in Table 1.

As indicated by arrow 604 in FIG. 8 and line 674 in FIG. 9, the detected fetal heart rate is further transmitted to heartbeat coincidence detector 562. Heartbeat coincidence detector 562 determines the coincidence between the detected heart rate across the entire depth range (received from fetal heart rate detector 1 (554) as indicated by arrow 592) and the detected heart rate across each of the depth range subsets (received from fetal heart rate detector 2 (554) as indicated by arrow 604). In one implementation, the signals for each depth range subset transmitted across channel 2 are evaluated with respect to a corresponding segment of signals transmitted across channel 1 (the entire range scan). As indicated by line 676 in FIG. 9, the detected coincidence for each of the depth range subsets is transmitted to range selector 564.

According to one implementation, the coincidence between the detected heart rates is determined as follows:
1) E[j]=sum (absolute_value (HR1_330_$x$[i+j]−HR2_$x$[i]), i=0 . . . 40−1), j=0 . . . 8
   Where:
   a) x=39, 612, 915, 1218, 1521, 1824, 2127, 2430
   b) HR1_330_$x$[i], i=0 . . . 48−1
   c) 48[sample]=12[s]*4[sample/s]
   d) 12[s]–length of segment HR1_330_$x$
   e) 4[sample/s]–FHR output sample rate
   f) HR2_$x$[i], i=0 . . . 40−1
   g) 40[sample]=10[s]*4[sample/s]

h) 10[s]–length of segment HR2_x
i) segments HR1_330_x and HR2_x are aligned as shown on "Control flow diagram: scan mode in details"
2) Emin=min (E[j], j=0 . . . 8)
3) If Emin<Threshold then HBCx=1 else HBCx=0

Once the depth range selector 564 (TD selector) has received all the information from heartbeat coincidence detector 562 and signal quality detector 558, range selector 564 identifies those adjacent zones with signal coincidence and strength or signal quality. The boundaries of such adjacent zones as well as overlapping regions are used to define a fetal heart window 152 such as described above with respect to step 206 and FIG. 4. The selected range of abdominal depths to use for monitoring of the fetal heart or the window to be used for monitoring the fetal heart is stored in memory 566.

According to one example implementation, the pair of adjacent depth zones is selected by selector 564 as follows:
1) Xmax1=get_x_of_max_element (SQD2_x*HBCx, x=39, 612, 915, 1218, 1521, 1824, 2127, 2430)
2) Xmax2=get_x_of_max_element (SQD2_x*HBCx, x=39, 612, 915, 1218, 1521, 1824, 2127, 2430 excluding x=Xmax1)
3) Select TDy according to Table 2

TABLE 2

| | | | | | Xmax2 | | | | |
|---|---|---|---|---|---|---|---|---|---|
| | | 39 | 612 | 915 | 1218 | 1521 | 1824 | 2127 | 2430 | no Xmax2 |
| Xmax1 | 39 | | TD3_12 | TD3_30 | TD3_30 | TD3_30 | TD3_30 | TD3_30 | TD3_30 | TD3_30 |
| | 612 | TD3_12 | | TD6_15 | TD3_30 | TD3_30 | TD3_30 | TD3_30 | TD3_30 | TD3_30 |
| | 915 | TD3_30 | TD6_15 | | TD9_18 | TD3_30 | TD3_30 | TD3_30 | TD3_30 | TD3_30 |
| | 1218 | TD3_30 | TD3_30 | TD9_18 | | TD12_21 | TD3_30 | TD3_30 | TD3_30 | TD3_30 |
| | 1521 | TD3_30 | TD3_30 | TD3_30 | TD12_21 | | TD15_24 | TD3_30 | TD3_30 | TD3_30 |
| | 1824 | TD3_30 | TD3_30 | TD3_30 | TD3_30 | TD15_24 | | TD18_27 | TD3_30 | TD3_30 |
| | 2127 | TD3_30 | TD3_30 | TD3_30 | TD3_30 | TD3_30 | TD18_27 | | TD21_30 | TD3_30 |
| | 2430 | TD3_30 | TD3_30 | TD3_30 | TD3_30 | TD3_30 | TD3_30 | TD21_30 | | TD3_30 |
| | no Xmax1 | | | | | | | | | TD3_30 |

Figure 10:
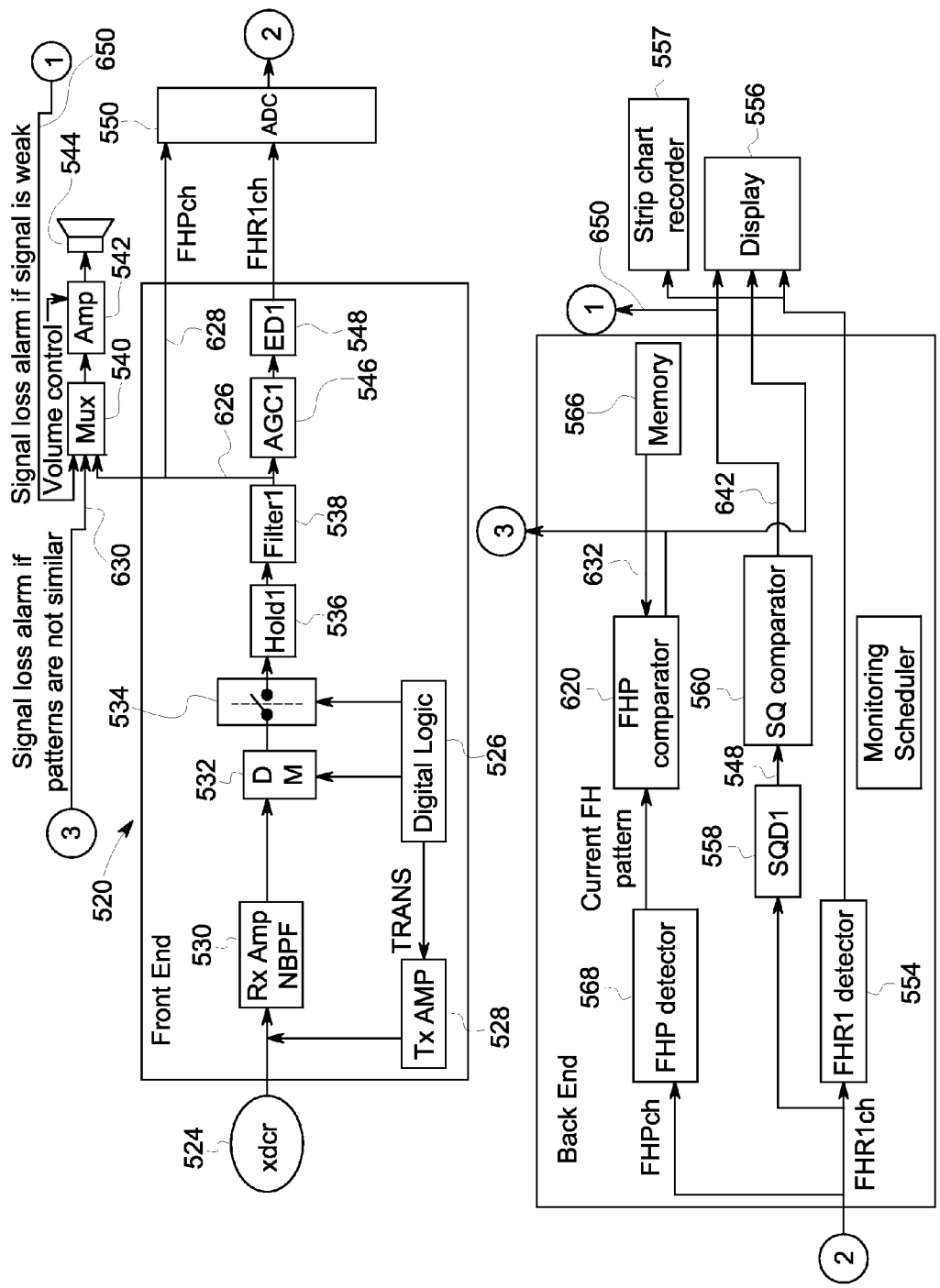
FIG. 10 is a diagram schematically illustrating those components of the fetal heart monitoring system of FIG. 8 employed during the correlation mode.

As shown by FIG. 7, once fetal heart window 152 (TDx) (shown in FIG. 3) has been identified, continuous monitoring the fetal heart may begin with fetal heart monitoring system 520 entering into a monitoring mode MM. FIG. 10 schematically illustrates components of fetal heart monitoring system 520 employed during the monitoring mode MM. As shown by FIG. 10, during the monitoring mode, fetal heart monitoring system 520 additionally employs fetal heart pattern comparator 620. In operation, digital logic 526 generates ultrasound transmit tone signals focused on the selected window 152 which are amplified by amplifier 528.

Figure 10A:
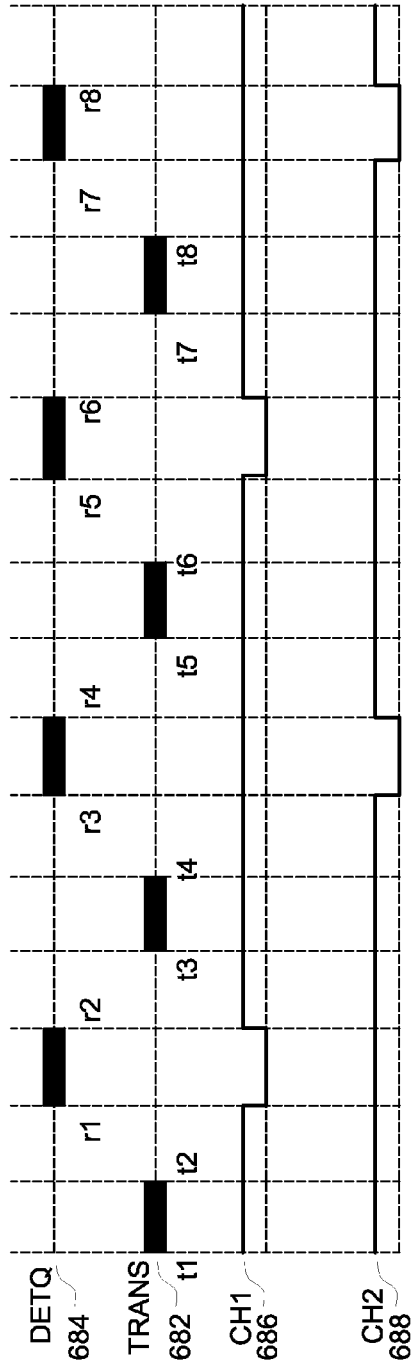
FIG. 10A is an example timing diagram illustrating the transmission and receiving of ultrasound signals with respect to the fetal heart window during fetal heart monitoring.

FIG. 10A is a timing diagram with its associated timing tables illustrating one example of such ultrasound penetration range during such fetal heart monitoring. As shown by FIG. 10A, digital logic 526 and amplifier 528 cause transmit tone signals 682 to be emitted by transducer 524, wherein such embedded transmit tone signals 682 are directed at the selected fetal heart window or range. As shown by line 682 in FIG. 10A, tones t1-t4, t3-t4, t5-t6 and so on are directed at the selected range of window 152 while system 520 is in the monitoring mode. Transducer 524 receives echo signals in a similar fashion. As shown by line 684, transducer 524 receives the echo signals from the selected range within intervals r1-r2, r3-r4 and so on. The received echo signals are amplified by amplifier 530 and demodulated by demodulator 532. As shown by CH11 line 686, such received echo signals are processed across channel 1. As shown by CH1 line 688, signals are not transmitted across channel 2 to during monitoring mode.

As shown by FIG. 8, such monitored signals undergo further signal processing prior to being evaluated by the lower portion of a system 520 shown in FIG. 10. As shown in the upper portion of FIG. 10, such monitored signals are stored by sample and hold capacitor Hold 1 (536) and filtered by band pass filter 1 (538). As indicated by arrow 626, the filtered signals are transmitted to multiplexer 540, amplified by amplifier 542 and output by speaker 544. As indicated by arrow 628, the filtered signals are further directly transmitted across a fetal heart pattern channel (FHPch) directly to analog-to-digital converter 550 and to fetal heart pattern detector 568. The filtered signals are further transmitted to automatic gain control 1 (546) and to envelope detector 1 (548) along fetal heart rate 1 channel (FHR1ch) prior to being transmitted to analog-to-digital converter 550 across the fetal heart rate 1 channel (FHR1ch). In other implementations, one or more of the illustrated analog components may be replaced with digital components or software implemented by one or more processors.

As shown in the bottom half of FIG. 10, the digital signals based upon the monitored ultrasound echo signals are transmitted to the FHR1 detector (554) which detects the fetal heart rate and transmits its output to display 556 and recorder 557. The digital signals transmitted along fetal heart pattern channel (FHPch) are transmitted to fetal heart pattern detector 568 which outputs the current fetal heart pattern to fetal heart pattern comparator 620. As indicated by arrow 632, fetal heart pattern comparator further takes as input the reference fetal heart pattern stored in memory 566. Fetal heart pattern comparator 620 compares the current fetal heart pattern of the monitored signals with the reference fetal heart pattern once per e.g., 1 minute.

In one implementation, to determine if the pattern of the monitored signals sufficiently corresponds to the pattern of the reference signals, fetal heart pattern comparator 620 evaluates the comparison against a predefined matching threshold stored in memory 566. The threshold has a value selected such that the threshold is low enough to be exceeded despite changes in the monitored set of ultrasound echo signals merely due to fetal heart angular orientation changes, avoiding false alarms. At the same time, the threshold has a value that is high enough so as to not be exceeded when changes in the monitored set of ultrasound echo signals are due to worsening fetal conditions or due to the influence maternal or fetal movements that cause the transducer 24 to undesirably lock onto unwanted maternal abdominal vessels.

In one example, an averaged amplitude spectrum of the fetal heartbeat is used as a pattern of the reference signals against which the monitored signals are compared. In one implementation, a correlation coefficient is utilized as a measure of similarity between the monitored signals and the reference signals. In one example, an averaged amplitude spectrum is obtained from the monitored signals at each 10 second interval with a sampling rate of 2 ksps. The correlation coefficient is a Pearson correlation coefficient. As indicated by arrow 630, if the coefficient is below the threshold, the alarm signal is transmitted to multiplexer 540, wherein alarm signal amplified by amplifier 542 and output by speaker 544 to alert a caretaker to the loss of a fetal heart signal and possible lock on maternal abdominal vessels. As indicated by arrow 642, the alarm signals are further transmitted to display 556, further visually notifying the caretaker. In other examples, the correlation or matching between the reference signals and the monitored signals may be made using other patterns, other sampling rates and other correlation coefficients.

As shown by FIG. 7, upon the alarm being output at time 690 and upon the caretaker determining that the health of the fetus is not at risk, the caretaker may adjust the positioning of transducer 524 to resume reliable monitoring of the fetal heart. In particular, the caretaker a once again reinitiate the transducer positioning search mode (TPS), repeating the same steps as discussed above when the transducer was initially positioned against the abdomen for the first time. Once the transducer 524 has been positioned at a location which the caretaker visibly and audibly determines the strongest signals are being received by transducer 524, the caretaker may enter instructions by keypad 570 discontinuing the TPS mode. As result, scan scheduler 572 causes monitoring system 520 to once again enter a scanning mode SM (shown in FIG. 7 and FIG. 9), either automatically or in response to a command entered by the caretaker using keypad 570. The scanning mode is performed as described above until a desired window or range 152 has been selected for further monitoring. Once a window has been identified, monitoring of the fetal heart using the window in the monitoring mode MM is reinitiated. This cycle of monitoring, outputting alarm, repositioning the transducer, re-identifying a fetal heart window and once again monitoring the fetal heart using the newly identified the fetal heart window is continuously repeated during the monitoring of the fetal heart by system 520.

Figure 12:
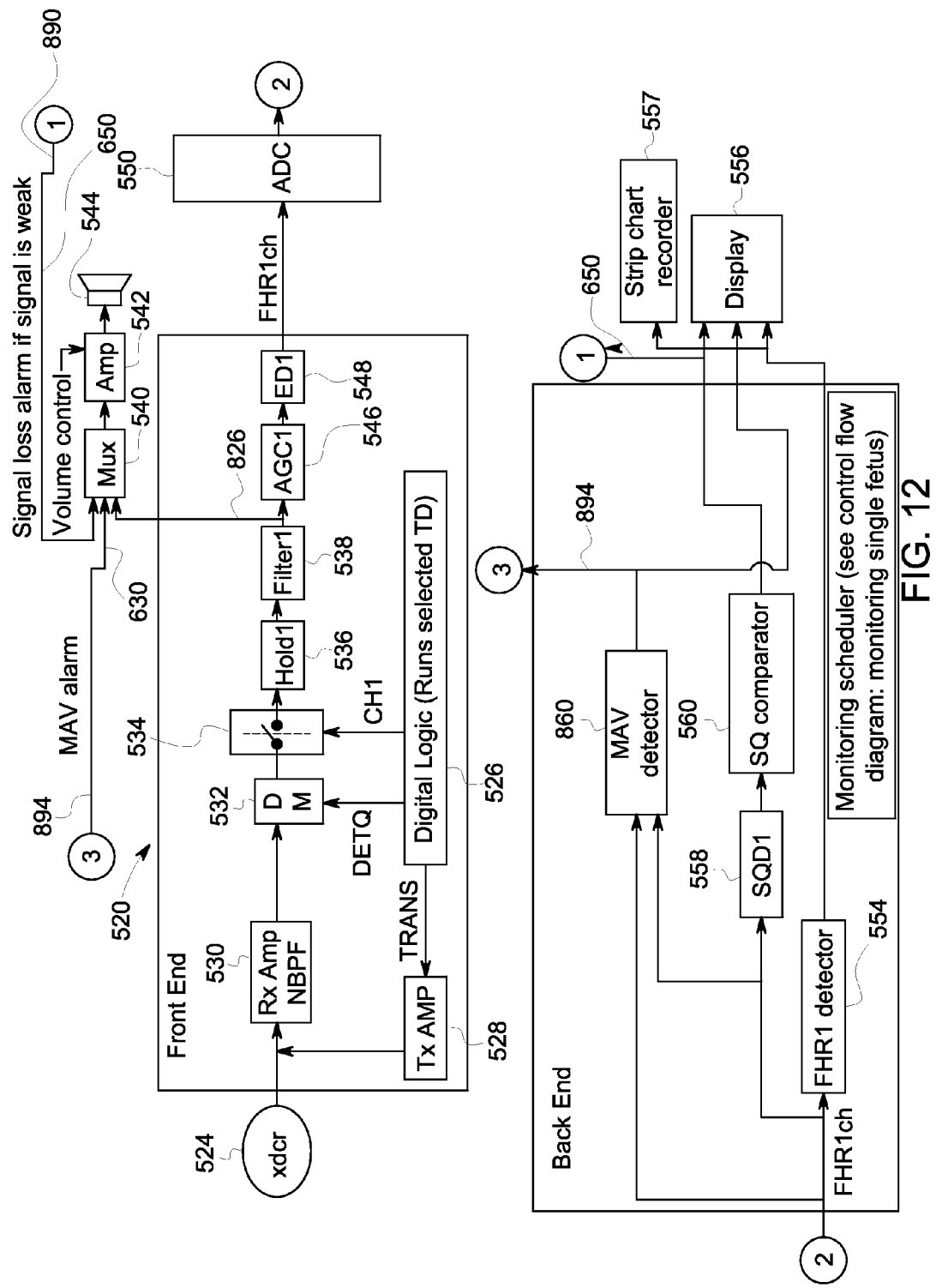
FIG. 12 is a diagram schematically illustrating those components of the fetal heart monitoring system of FIG. 8 employed during the cancellation mode.

FIG. 11 is a control flow diagram illustrating an example method 700 for monitoring a single fetus. Method 700 is similar to method 400 (shown in FIG. 7) except the method 700 detects the influence of a sensed maternal pulse utilizing the generally described cancellation mode 110 (shown in FIG. 2). FIG. 12 schematically illustrates those portions of fetal monitoring system 520 that are utilized with this alternative cancellation mode 110 during monitoring of a fetal heart. In other implementations where fetal monitoring system 520 is configured to perform only one of the fetal pattern correlation mode 108 or the fetal signal cancellation mode 110, those components illustrated in FIGS. 8, 10 and 12 which are not used in the single mode employed may be omitted. For example, in implementations where only the cancellation mode is offered, fetal heart pattern detector 568, memory 566 for storing the reference pattern may be omitted. The fetal heart pattern comparator 620 is replaced by a maternal abdominal vessels (MAV) signal detector.

As shown by FIG. 11, in method 700, the caretaker locates transducer 524, in the same manner as described above with respect to method 400. Likewise, in method 700, the fetal heart window 152 is identified in the same manner as described above with respect to method 400. However, in contrast to method 400, once the fetal heart window 152 has been identified or selected, as indicated by line 702 in FIG. 11, maternal abdominal vessel detection is carried out to determine whether the current positioning of transducer 524 results in window 152 being influenced by a maternal pulse or signals resulting from a maternal abdominal vessel (MAV).

As shown by FIG. 12, during such maternal abdominal vessel detection, digital logic 526 generates ultrasound transmit tone signals focused on the selected window 152 which are amplified by amplifier 528. The reflected echo signals from the window 152 are subsequently received by transducer 524 and amplified by amplifier 530. Such signals are further demodulated by demodulator 532 and transmitted across channel 1 (534) for further signal processing. In particular, such monitored signals are stored by sample and hold capacitor 1 hold 1 (536) and filtered by band pass filter 1 (538). As indicated by arrow 826, the filtered signals are transmitted to multiplexer 540, amplified by amplifier 542 and output by speaker 544. The filtered signals are further transmitted to automatic gain control 1 (546) and to envelope detector 1 (548) along fetal heart rate 1 channel (FHR1$ch$) prior to being transmitted to analog-to-digital converter 550 across the fetal heart rate 1 channel (FHR1$ch$). In other implementations, one or more of the illustrated analog components may be replaced with digital components or software implemented by one or more processors.

As shown in the bottom half of FIG. 12, the digital signals based upon the monitored ultrasound echo signals are transmitted to the fetal heart rate 1 detector (554) which detects the fetal heart rate and transmits its output to display 556 and recorder 557. As indicated by arrow 828, fetal heart rate signals are further transmitted to signal quality detector 1 (558) and MAV detector 860. Signal quality detector 1 (558) detects the signal quality. The detected signal quality is transmitted to signal quality comparator 560 which performs real-time evaluation of the power of the signal by comparing the power to a predetermined threshold. The signal quality measure is transmitted to display 556. As indicated by arrow 890, if single quality is poor (as determined by the value with respect to the predetermined threshold), a signal loss alarm is transmitted to multiplexer 540, whereby an audible alarm is transmitted using amplifier 542 and speaker 544.

Figure 13:
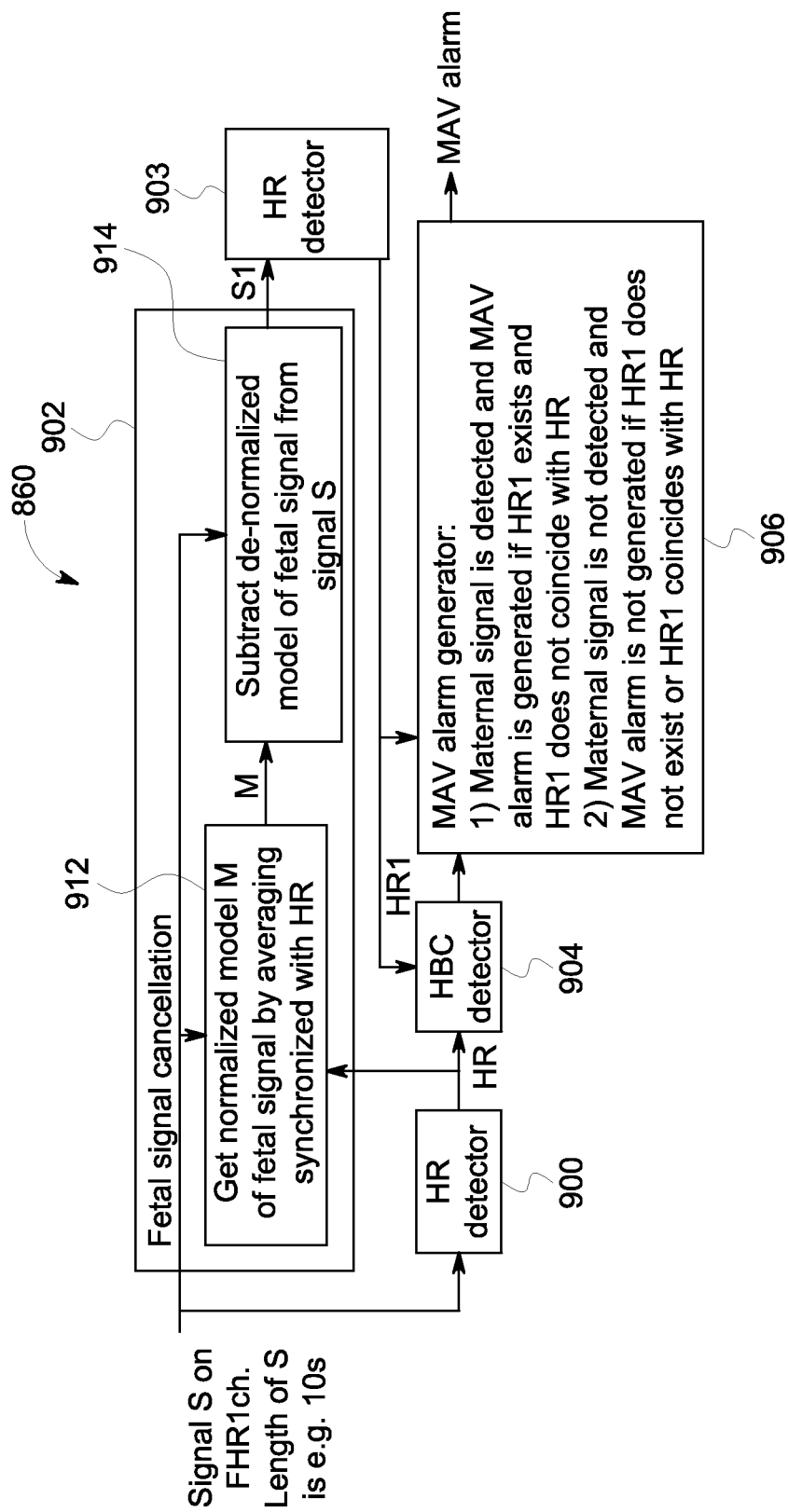
FIG. 13 is a flow diagram of an example method for identifying the influence of maternal signals.

FIG. 13 schematically illustrates MAV detector 860 in more detail. As shown by FIG. 13, MAV detector 860 comprises heart rate detector 900, cancellation module 902, remaining signal heart rate detector 903, heart beat coincidence detector 904, and alarm generator 906. MAV detector 860 receives a sample of a monitored signal for predefined period of time (10 seconds in the example illustrated). This signal is transmitted to cancellation module 902 and to heart rate detector 900. HR detector 900 detects the heart rate from such raw signals and transmits the output heart rate HR to heartbeat coincidence detector 904.

Cancellation module 902 carries out the cancellation method 300 (shown in FIG. 5). In particular, as indicated by block 912, fetal signal cancellation module 902 executes blocks 302-312 shown on FIG. 5 to get normalized model M of fetal signal. As indicated by block 914, module 902 executes block 314 shown on FIG. 5 to get composite signal S1 after fetal signal cancellation (referred to as remaining signal). The remaining signal S1 is transmitted to remaining signal heart rate detector 903 which determines the existence of heart beat rate HR1 of the remaining signal and transmits heart rate HR1 to heartbeat coincidence detector 904. Heartbeat coincidence detector 904 evaluates a degree or level of coincidence between the heart rate HR1 and the heart rate HR received from heart rate detector 900. As indicated in FIG. 13, MAV alarm generator 906 generates an alarm if the fetal heart rate HR1 exists and does not satisfy a predefined degree of coincidence with the fetal heart rate HR. In one implementation, to satisfy the predefined degree of coincidence, the difference between HR and HR1 must be less than a threshold of five heartbeats per minute. In other implementations, other thresholds may be employed. As indicated by arrow 894 in FIG. 12, the alarm signal is transmitted to multiplexer 540, where the alarm signal is amplified by amplifier 542 and output by speaker 544. Alternatively, if the heart rate HR1 does not exist or does not satisfy a predefined degree of coincidence with HR, the maternal signal is not detected and the alarm is not sounded.

In the example scenario illustrated in FIG. 11, the initial positioning of transducer 524 results in a MAV alarm being sounded as indicated by step 706. As a result, the caretaker reinitiates the transducer position search mode and repositions the transducer. As indicated by step 708 and 710, the scan mode is also carried out identifying a new HR window 152 at the new location of the transducer 524. As indicated by step 712, the MAV detection set forth above is carried out once again. However, in this instance, no MAV alarm is sounded. Thereafter, monitoring the fetal heart rate is continued. In the example scenario illustrated, as indicated at point 714, the alarm is once again sounded due to a signal loss (low signal quality identified by signal quality comparator 560 (shown in FIG. 12). As a result, the operator once again initiate the transducer position search mode and repositions the transducer 524. With such repositioning of the transducer 524, as indicated by step 716, the scan mode is once again carried out to identify a fetal heart window 152, which may be new or may be the same as the previous window 152. As a result of such repositioning, MAV detection is repeated. If the MAV detection results in an MAV alarm being output, the nurse is prompted to once again reposition transducer 542, initiating the process at step 706.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A method comprising:
    sensing multiple pairs of overlapping depth zones with an ultrasound transducer, each pair of overlapping depth zones having a first depth zone and a second depth zone, each of the first and second depth zones having at least one distance from the ultrasonic transducer that is not within the other of the first and second depth zones;
    comparing a strength of ultrasound signals from each pair of overlapping depth zones of the multiple pairs to strengths of other pairs of the multiple pairs;
    selecting a pair of overlapping depth zones from the multiple pairs of overlapping depth zones based on the comparison;
    determining an approximate distance between the ultrasonic transducer and a fetal heart based upon an overlapping portion of the selected pair of overlapping depth zones;
    sensing a monitoring window of distances from the ultrasonic transducer using the ultrasonic transducer, the monitoring window having a minimum distance based upon the approximate distance; and
    monitoring a heart rate of the fetal heart using ultrasonic echo signals from the monitoring window.

2. The method of claim 1, wherein the monitoring window has a maximum distance based on the approximate distance.

3. The method of claim 1, wherein the minimum distance of the monitoring window is spaced from the approximate distance by a spacing.

4. The method of claim 1, wherein the minimum distance of the monitoring window and the maximum distance of the monitoring window encloses and is spaced from the fetal heart.

5. The method of claim 1, wherein the selected pair of overlapping depth zones is at which strength of an echo signal is highest.

6. The method of claim 1, wherein the monitoring window has a minimum distance corresponding to a proximal shallower boundary of the selected pair of overlapping depth zones and wherein the monitoring window has a maximum distance corresponding to a distal deeper boundary of the selected pair of overlapping depth zones.

7. The method of claim 1, wherein the selected pair of overlapping depth zones is further selected based upon coincidence of heart rate detected on ultrasound signals reflected from the selected pair of overlapping depth zones with heart rate detected on ultrasound signals reflected from an entire range of all the multiple pairs of overlapping depth zones.

8. The method of claim 1 further comprising:
    acquiring a reference ultrasound signal from the fetal heart from the monitoring window;
    acquiring a monitored ultrasound signal from the monitoring window; and
    comparing a pattern of the monitored ultrasound signal to a pattern of the reference ultrasound signal to determine whether to output an alarm based on a similarity of the pattern of the reference ultrasound signal and the pattern of the monitored ultrasound signal.

9. The method of claim 8, wherein the comparison is correlation.

10. The method of claim 9 wherein the alarm is output if a value from the correlation is less than a predefined threshold.

11. The method of claim 10, wherein the predefined threshold is low enough to be exceeded despite changes in the monitored ultrasound echo signal due to fetal heart angular orientation changes and wherein the predefined threshold is high enough to not be exceeded when changes in the monitored ultrasound echo signal is due to one of ultrasound echo signals from maternal abdominal vessels and worsening fetal conditions.

12. A fetal heart monitoring system comprising:
    an ultrasonic transducer;
    a controller configured to generate control signals directing the operation of the ultrasonic transducer and to receive echo signals from the ultrasonic transducer, the controller configured to:

sense multiple pairs of overlapping depth zones, each pair of overlapping depth zones having a first depth zone and a second depth zone, each of the first and second depth zones having at least one distance from the ultrasonic transducer that is not in the other of the first and second depth zones;

compare a strength of ultrasound signals from each pair of overlapping depth zones of the multiple pairs to strengths of other pairs of the multiple pairs;

select a pair of overlapping depth zones from the multiple pairs of overlapping depth zones based on the comparison;

determine an approximate distance between an ultrasonic transducer and the fetal heart based upon an overlapping portion of the selected pair of overlapping depth zones;

sense a monitoring window of distances from the ultrasonic transducer using the ultrasonic transducer, the monitoring window having a minimum distance based upon the approximate distance; and monitor a heart rate of the fetal heart using ultrasonic echo signals from the monitoring window.

13. The fetal heart monitoring system of claim 12, wherein the selected pair of overlapping depth zones is at which strength of an echo signal is highest.

14. The fetal heart monitoring system of claim 12, wherein the controller is further configured to:
acquire a reference ultrasound signal from the fetal heart from the monitoring window;
acquire a monitored ultrasound signal from the monitoring window; and
compare a pattern of the monitored ultrasound signal to a pattern of the reference ultrasound signal to determine whether to output an alarm based on based on a similarity of the pattern of the reference ultrasound signal and the pattern of the monitored ultrasound signal.

15. The fetal heart monitoring system of claim 14, wherein the comparison is correlation.

16. The fetal heart monitoring system of claim 14 wherein the alarm is output if a value from the correlation is less than a predefined threshold.

17. An apparatus comprising:
a non-transient computer-readable medium containing computer-readable code to direct a processor to:
sense multiple pairs of overlapping depth zones, each pair of overlapping depth zones having a first depth zone and a second depth zone, each of the first and second depth zones having at least one distance from the ultrasonic transducer that is not in the other of the first and second depth zones;

determine an approximate distance between an ultrasonic transducer and the fetal heart based upon an overlapping portion of a selected pair of overlapping depth zones from the multiple pairs of overlapping depth zones, the selected pair being selected based upon coincidence of heart rate detected on ultrasound signals reflected from the selected pair of overlapping depth zones with heart rate detected on ultrasound signals reflected from an entire range containing all of the multiple pairs of overlapping depth zones;

sense a monitoring window of distances from the ultrasonic transducer using the ultrasonic transducer, the monitoring window having a minimum distance based upon the approximate distance; and monitor a heart rate of the fetal heart using ultrasonic echo signals from the monitoring window.

18. The apparatus of claim 17, wherein the non-transient computer-readable medium contains computer-readable code to direct a processor to:
acquire a reference ultrasound signal from the fetal heart from the monitoring window;
acquire a monitored ultrasound signal from the monitoring window; and
compare a pattern of the monitored ultrasound signal to a pattern of the reference ultrasound signal to determine whether to output an alarm based on based on a similarity of the pattern of the reference ultrasound signal and the pattern of the monitored ultrasound signal.

19. The apparatus of claim 18, wherein the comparison is correlation.

20. The apparatus of claim 18, wherein computer-readable code is configured to direct a processor to output the alarm is output if a value from the correlation is less than a predefined threshold.

* * * * *